(12) United States Patent
Yamamoto et al.

(10) Patent No.: US 7,833,150 B2
(45) Date of Patent: Nov. 16, 2010

(54) HOLDING DEVICE, ENDOSCOPIC DEVICE, AND OPERATING METHOD OF ENDOSCOPIC DEVICE

(75) Inventors: Hironori Yamamoto, Tochigi (JP); Mitsunori Machida, Saitama (JP); Yoshinori Kadouno, Saitama (JP); Masayuki Takano, Saitama (JP); Toshio Sakamoto, Saitama (JP); Tadashi Sekiguchi, Saitama (JP); Tetsuya Fujikura, Saitama (JP)

(73) Assignees: Fujifilm Corporation, Tokyo (JP); SRJ Corporation, Tochigi (JP)

( * ) Notice: Subject to any disclaimer, the term of this patent is extended or adjusted under 35 U.S.C. 154(b) by 956 days.

(21) Appl. No.: 11/094,568

(22) Filed: Mar. 31, 2005

(65) Prior Publication Data

US 2005/0234293 A1   Oct. 20, 2005

(30) Foreign Application Priority Data

Mar. 31, 2004 (JP) ............................. 2004-107179
Oct. 22, 2004 (JP) ............................. 2004-308690
Jan. 24, 2005 (JP) ............................. 2005-015711

(51) Int. Cl.
*A61B 1/00* (2006.01)
*A61B 1/04* (2006.01)

(52) U.S. Cl. ...................... 600/102; 600/115; 600/116; 600/118; 600/124

(58) Field of Classification Search ................. 600/102, 600/114–116, 119, 121–125, 227, 228, 231; 604/95.03
See application file for complete search history.

(56) References Cited

U.S. PATENT DOCUMENTS

| | | | | |
|---|---|---|---|---|
| 4,040,413 A * | 8/1977 | Ohshiro | ...................... | 600/116 |
| 4,461,182 A * | 7/1984 | Jones et al. | .............. | 73/862.53 |
| 4,573,452 A | 3/1986 | Greenberg | | |
| 4,690,131 A * | 9/1987 | Lyddy et al. | ................. | 600/115 |
| 5,243,967 A * | 9/1993 | Hibino | ....................... | 600/109 |
| 5,540,649 A | 7/1996 | Bonnell et al. | | |
| 5,679,110 A * | 10/1997 | Hamazaki | .................... | 600/124 |
| 5,842,996 A * | 12/1998 | Gruenfeld et al. | ........... | 600/490 |
| 5,997,471 A | 12/1999 | Gumb et al. | | |
| 6,007,482 A * | 12/1999 | Madni et al. | ................. | 600/115 |
| 6,132,368 A * | 10/2000 | Cooper | ....................... | 600/102 |
| 6,451,027 B1 | 9/2002 | Cooper et al. | | |
| 6,833,912 B2 * | 12/2004 | Lei et al. | .................... | 356/124 |
| 2002/0177789 A1 * | 11/2002 | Ferry et al. | ................. | 600/585 |

FOREIGN PATENT DOCUMENTS

JP   51-11689   1/1976

* cited by examiner

*Primary Examiner*—Linda C Dvorak
*Assistant Examiner*—Alireza Nia
(74) *Attorney, Agent, or Firm*—Young & Thompson

(57) ABSTRACT

A hand operation portion of an endoscope is held by an endoscope holder of a holding device, and an insertion auxiliary member is held by an auxiliary member holder. The endoscope holder and the auxiliary member holder are slidably supported along a guide rail on a stage, and linearly moved toward a mouth of a patient.

6 Claims, 28 Drawing Sheets

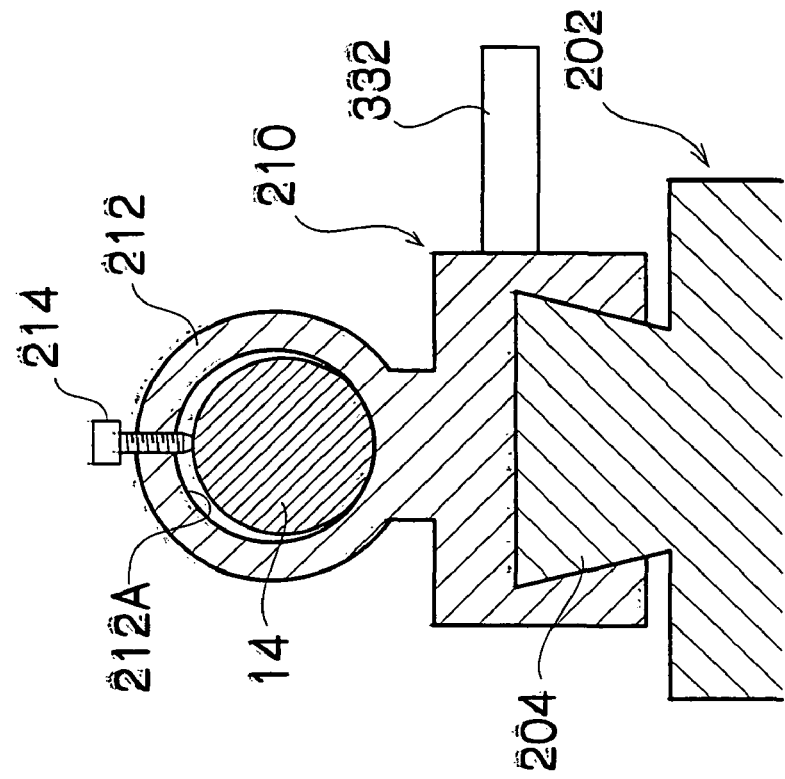
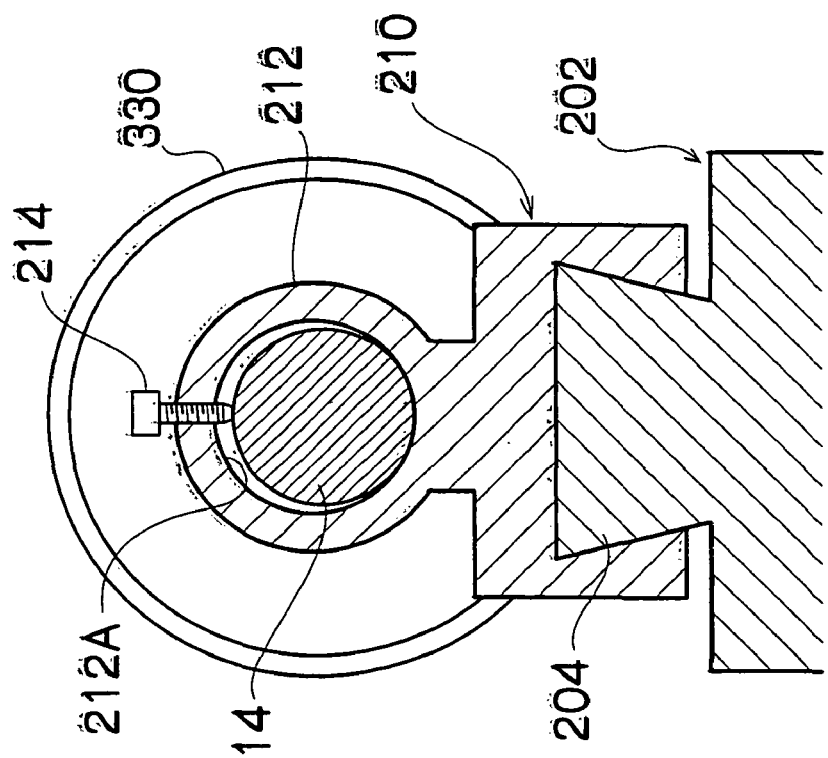

HOLDING DEVICE, ENDOSCOPIC DEVICE, AND OPERATING METHOD OF ENDOSCOPIC DEVICE

BACKGROUND OF THE INVENTION

1. Field of the Invention

The present invention relates to a holding device, an endoscopic device, and an operating method of the endoscopic device, and more particularly to a medical endoscopic device for observing an alimentary canal in a deep part such as small intestine or large intestine.

2. Description of the Related Art

A medical endoscope has an insertion portion to be inserted into a patient, and the insertion portion is inserted through the mouth or anus of the patient to observe stomach, duodenum or large intestine. In observation of small intestine, however, insertion of a tip of the insertion portion into a deep part of the small intestine is difficult in simple insertion of the insertion portion, because the small intestine is situated far away from the mouth or anus and an alimentary canal to the small intestine is bent in a complex manner. Thus, a method is proposed for inserting an insertion portion of an endoscope covered with an insertion auxiliary member into a body cavity, and guiding the insertion portion with the insertion auxiliary member to prevent surplus bending or flection of the insertion portion.

Japanese Patent Application Laid-open No. 51-11689 discloses an endoscopic device comprising an endoscope and an insertion auxiliary member (also referred to as an over tube or a sliding tube) covered over the insertion portion of the endoscope to help insertion. This endoscopic device comprises a first balloon at a tip of the insertion portion, and a second balloon at a tip of the insertion auxiliary member, and alternately inserts the insertion portion and the insertion auxiliary member while repeating expansion and contraction of the first balloon and the second balloon, thereby allowing the insertion portion to be inserted into a deep part of intestine with complex bending such as small intestine.

SUMMARY OF THE INVENTION

The conventional endoscopic device requires that an operator grips a hand operation portion of an endoscope for operation, while an assistant grips an insertion auxiliary member for operation. The conventional endoscopic device thus cannot be operated without the assistant. Further, the conventional endoscopic device requires that the operator and the assistant operate at the same timing, and the operator and also the assistant need to have skills.

For the conventional endoscopic device, the insertion portion of the endoscope and the insertion auxiliary member cannot be smoothly inserted into or removed from a patient when the insertion portion and the insertion auxiliary member are pushed or pulled, which may place unnecessary burdens on the patient.

The invention has been achieved in view of the above described circumstances, and has an object to provide a holding device for an endoscopic device that improves operability of an endoscope and an insertion auxiliary member, an endoscopic device comprising the holding device, and an operating method of the endoscopic device.

In order to achieve the above described object, a first aspect of the invention provides a holding device comprising a holder which holds at least one of an endoscope and an insertion auxiliary member that is placed over an insertion portion of the endoscope to help insertion of the insertion portion.

According to the first aspect, the endoscope and/or the insertion auxiliary member is held by the holder, thereby improving operability of the endoscope and/or the insertion auxiliary member. Specifically, the insertion auxiliary member is held by the holder to allow an operator to push and pull the endoscope by himself/herself. Likewise, the endoscope is held by the holder to allow the operator to push and pull the insertion auxiliary member by himself/herself. Further, both the endoscope and the insertion auxiliary member are held by the holder to allow the operator to operate a peripheral device such as a light source device or a processor, or an endoscopic treatment tool such as forceps with his/her free hand.

In a second aspect of the invention according to the first aspect, the holder restricts movement of the endoscope and/or the insertion auxiliary member. Thus, according to the second aspect, the endoscope and/or the insertion auxiliary member is restricted in a predetermined direction to allow the endoscope and/or the insertion auxiliary member to be smoothly moved in the predetermined direction. This allows the endoscope and the insertion auxiliary member to be pushed and pulled without placing burdens on a patient.

In a third aspect of the invention according to the first or the second aspect, the holder holds the endoscope and/or the insertion auxiliary member movably in an insertion direction of the insertion portion of the endoscope. Thus, according to the third aspect, the endoscope and/or the insertion auxiliary member can be moved in the insertion direction while being held by the holder. This allows the endoscope and/or the insertion auxiliary member to be moved in the insertion direction without an unnecessary force being applied to the endoscope and/or the insertion auxiliary member, and allows the endoscope and/or the insertion auxiliary member to be smoothly inserted into the patient, thereby reducing burdens on the patient.

In a fourth aspect of the invention according to the third aspect, the holder is capable of securing the endoscope and/or the insertion auxiliary member at any position in the insertion direction of the insertion portion of the endoscope. Thus, according to the fourth aspect, the endoscope and/or the insertion auxiliary member can be inserted a desired distance into the patient and then held.

In a fifth aspect of the invention according to the first to the fourth aspects, the holder holds the endoscope and/or the insertion auxiliary member movably in a direction other than the insertion direction of the insertion portion of the endoscope. Thus, according to the fifth aspect, a position of the endoscope and/or the insertion auxiliary member can be freely adjusted. The insertion direction of the endoscope and/or the insertion auxiliary member can be also freely adjusted.

In a sixth aspect of the invention according to the fifth aspect, the holder is capable of securing the endoscope and/or the insertion auxiliary member at any position in the direction other than the insertion direction of the insertion portion of the endoscope. Thus, according to the sixth aspect, the endoscope and/or the insertion auxiliary member can be held at any position.

In a seventh aspect of the invention according to any one of the third to the sixth aspects, the holding device further comprises a driving device which moves the holder. Thus, according to the seventh aspect, the endoscope and/or the insertion auxiliary member can be automatically moved by the driving device.

In an eighth aspect of the invention according to the seventh aspect, the holding device further comprises a control device which controls the driving device so as to move the holder in the insertion direction of the insertion portion of the endoscope. Thus, according to the eighth aspect, the endoscope and/or the insertion auxiliary member can be automatically inserted.

In a ninth aspect of the invention according to the seventh aspect, the holding device further comprises a control device which controls the driving device so as to move the holder in the direction other than the insertion direction of the insertion portion of the endoscope. Thus, according to the ninth aspect, the position and the insertion direction of the endoscope and/or the insertion auxiliary member can be automatically adjusted.

In a tenth aspect of the invention according to any one of the first to the ninth aspects, the holding device further comprises an insertion length measurement device which measures an insertion length of the insertion portion of the endoscope and/or the insertion auxiliary member. Thus, according to the tenth aspect, the insertion length of the endoscope and/or the insertion auxiliary member can be recognized, thereby allowing control of the insertion length.

In an eleventh aspect of the invention according to any one of the first to the tenth aspects, the holding device further comprises a load measurement device which measures a load generated when the endoscope and/or the insertion auxiliary member is moved. Thus, according to the eleventh aspect, the load when the endoscope and/or the insertion auxiliary member is moved can be recognized.

In a twelfth aspect of the invention according to the eleventh aspect, the holding device further comprises a safety device that is actuated based on a measurement value of the load measurement device. Thus, according to the twelfth aspect, the load generated when the endoscope and/or the insertion auxiliary member is moved is prevented from increasing to place burdens on the patient.

In a thirteenth aspect of the invention according to any one of the first to the twelfth aspects, the holder comprises an endoscope holder which holds the endoscope and an auxiliary member holder which holds the insertion auxiliary member, and an extendable cover which prevents a splash of a body fluid from a body cavity is mounted in a surrounding manner at least between the endoscope holder and the auxiliary member holder. Thus, according to the thirteenth aspect, the cover can prevent a splash of a liquid such as a body fluid from the insertion portion and/or a base end portion of the insertion auxiliary member. Also, according to the thirteenth aspect, the cover is adapted to be extendable, thereby allowing the endoscope and/or the insertion auxiliary member to be moved with the cover being attached.

In a fourteenth aspect of the invention according to any one of the first to the thirteenth aspects, the holding device further comprises a securing device which secures the holder to a different member. Thus, according to the fourteenth aspect, the holding device can be secured to another securing device and used.

In a fifteenth aspect of the invention according to any one of the first to the fourteenth aspects, an expandable balloon is mounted to a tip of the insertion portion of the endoscope and/or a tip of the insertion auxiliary member. When the expandable balloon is mounted, the endoscope and the insertion auxiliary member are moved one by one, and thus the endoscope and/or the insertion auxiliary member is held by the holding device to significantly improve operability.

In order to achieve the above described object, a sixteenth aspect of the invention provides an endoscopic device, comprising: an endoscope having an expandable first balloon at a tip of an insertion portion; and an insertion auxiliary member that is placed over the insertion portion of the endoscope to help insertion of the insertion portion and has a second balloon at a tip of the insertion auxiliary member, wherein the endoscopic device comprises a holding device according to the first to the fourteenth aspects which holds the endoscope and/or the insertion auxiliary member. Thus, according to the sixteenth aspect, the endoscope and/or the insertion auxiliary member is held by the holding device to eliminate the need for an operator to grip the endoscope and/or the insertion auxiliary member, thereby allowing an operation by the operator by himself/herself. For an endoscopic device of a double balloon type having the first balloon at the endoscope and the second balloon at the insertion auxiliary member, the endoscope and the insertion auxiliary member are often moved one by one, and thus the endoscope and/or the insertion auxiliary member is held by the holding device to significantly improve operability.

In order to achieve the above described object, a seventeenth aspect of the invention provides an operating method of an endoscopic device comprising an endoscope and an insertion auxiliary member that is placed over an insertion portion of the endoscope to help insertion of the insertion portion, wherein at least one of the endoscope and the insertion auxiliary member is held by a holding device. Thus, according to the seventeenth aspect, at least one of the endoscope and the insertion auxiliary member is held by the holding device to significantly improve operability and allow an operation by an operator by himself/herself. Specifically, the insertion auxiliary member is held by the holding device to allow the operator to push and pull the endoscope by himself/herself. Likewise, the endoscope is held by the holding device to allow the operator to push and pull the insertion auxiliary member by himself/herself. Further, both the endoscope and the insertion auxiliary member are held by the holding device to allow the operator to operate a peripheral device such as a light source device or a processor, or an endoscopic treatment tool such as forceps.

In order to achieve the above described object, an eighteenth aspect of the invention provides an operating method of an endoscopic device for inserting, into a tubular body cavity, an endoscope having an expandable first balloon at a tip of an insertion portion, and an insertion auxiliary member that is placed over the insertion portion of the endoscope to help insertion of the insertion portion and has an expandable second balloon at a tip of the insertion auxiliary member, successively comprising the steps of: inserting the insertion portion and the insertion auxiliary member into the tubular body cavity with the first balloon and the second balloon being contracted, and then expanding the second balloon to secure the insertion auxiliary member in the tubular body cavity; inserting the insertion portion into a deeper part of the tubular body cavity with the guide of the insertion auxiliary member; expanding the first balloon to secure the insertion portion in the tubular body cavity; contracting the second balloon to insert the insertion auxiliary member with the guide of the insertion portion; expanding the second balloon to secure the insertion auxiliary member in the tubular body cavity; and drawing the insertion auxiliary member together with the insertion portion with the insertion auxiliary member being secured in the tubular body cavity, wherein at least one of the endoscope and the insertion auxiliary member is held by a holding device in each step. Thus, according to the eighteenth aspect, at least one of the endoscope and the insertion auxiliary member is held by the holding device in each step to significantly improve operability and allow an operation by an operator by himself/herself.

In order to achieve the above described object, a nineteenth aspect of the invention provides an operating method of an endoscopic device for inserting, into a tubular body cavity, an endoscope having an expandable first balloon at a tip of an insertion portion, and an insertion auxiliary member that is placed over the insertion portion of the endoscope to help insertion of the insertion portion and has an expandable second balloon at a tip of the insertion auxiliary member, wherein the operating method successively comprises the steps of: holding the endoscope and/or the insertion auxiliary member by a holding device, inserting the insertion portion and the insertion auxiliary member into the tubular body cavity with the first balloon and the second balloon being contracted, and then expanding the second balloon to secure the insertion auxiliary member in the tubular body cavity; inserting the insertion portion into a deeper part of the tubular body cavity with the guide of the insertion auxiliary member; expanding the first balloon to secure the insertion portion in the tubular body cavity; contracting the second balloon to insert the insertion auxiliary member with the guide of the insertion portion by the holding device; expanding the second balloon to secure the insertion auxiliary member in the tubular body cavity; and drawing the insertion auxiliary member together with the insertion portion with the insertion auxiliary member being secured in the tubular body cavity. Thus, according to the nineteenth aspect, the insertion auxiliary member can be automatically inserted.

In order to achieve the above described object, a twentieth aspect of the invention provides an operating method of an endoscopic device for inserting, into a tubular body cavity, an endoscope having an expandable first balloon at a tip of an insertion portion, and an insertion auxiliary member that is placed over the insertion portion of the endoscope to help insertion of the insertion portion and has an expandable second balloon at a tip of the insertion auxiliary member, wherein the operating method successively comprises the steps of: holding the endoscope and the insertion auxiliary member by a holding device, inserting the insertion portion and the insertion auxiliary member into the tubular body cavity by the holding device with the first balloon and the second balloon being contracted, and then expanding the second balloon to secure the insertion auxiliary member in the tubular body cavity; inserting the insertion portion into a deeper part of the tubular body cavity with the guide of the insertion auxiliary member by the holding device; expanding the first balloon to secure the insertion portion in the tubular body cavity; contracting the second balloon to insert the insertion auxiliary member with the guide of the insertion portion by the holding device; expanding the second balloon to secure the insertion auxiliary member in the tubular body cavity; and drawing the insertion auxiliary member together with the insertion portion by the holding device with the insertion auxiliary member being secured in the tubular body cavity. Thus, according to the twentieth aspect, the endoscope and the insertion auxiliary member can be automatically moved.

In order to achieve the above described object, a twenty-first aspect of the invention provides a holding device, comprising: a case of the holding device mounted to an insertion auxiliary member that is placed over an insertion portion of an endoscope to help insertion of the insertion portion; a roller that is rotatably supported by the case of the holding device and abutted against the insertion portion passed through the insertion auxiliary member; and a motor which rotates the roller.

According to the twenty-first aspect, a body of the holding device is mounted to the insertion auxiliary member, and the roller supported by the body is abutted against the insertion portion, thereby causing the endoscope to be held by the insertion auxiliary member via the holding device. Thus, an operator can grip one of the endoscope and the insertion auxiliary member to hold both the endoscope and the insertion auxiliary member, thereby improving operability and allowing the operator to operate the endoscope and/or the insertion auxiliary member by himself/herself.

Also, according to the twenty-first aspect, the roller abutted against the insertion portion is rotated by the motor to allow the insertion portion to be moved relative to the insertion auxiliary member. Thus, the endoscope or the insertion auxiliary member can be automatically inserted and removed.

In a twenty-second aspect of the invention according to the twenty-first aspect, the holding device further comprises an urging device which urges the roller toward the insertion portion. According to the twenty-second aspect, the roller is urged toward the insertion portion to allow the roller to be always abutted against the insertion portion, and the rotation of the roller ensures movement of the insertion portion with respect to the insertion auxiliary member. Further, the urged roller is abutted against the insertion portion to reduce resistance when the insertion portion is inserted into and removed from the insertion auxiliary member.

In order to achieve the above described object, a twenty-third aspect of the invention provides a holding device, comprising: a case of the holding device secured to an examination table; a roller that is rotatably supported by the case of the holding device, and abutted against an insertion portion of an endoscope or an insertion auxiliary member that is placed over the insertion portion to help insertion of the insertion portion; and a motor which rotates the roller.

According to the twenty-third aspect, a body of the holding device is secured to a different member, and the roller supported by the body is abutted against the insertion portion or the insertion auxiliary member, thereby causing the endoscope or the insertion auxiliary member to be held via the holding device. This allows an operator to operate the endoscope and/or the insertion auxiliary member by himself/herself.

Also, according to the twenty-third aspect, the roller abutted against the insertion portion or the insertion auxiliary member is rotated by the motor to allow movement of the insertion portion or the insertion auxiliary member. Thus, the endoscope or the insertion auxiliary member can be automatically inserted into and removed from a body cavity.

In a twenty-fourth aspect of the invention according to the twenty-third aspect, the holding device further comprises an urging device which urges the roller toward the insertion portion or the insertion auxiliary member. According to the twenty-fourth aspect, the roller is urged toward the insertion portion or the insertion auxiliary member to allow the roller to be always abutted against the insertion portion or the insertion auxiliary member, and the rotation of the roller ensures movement of the insertion portion or the insertion auxiliary member. Further, the urged roller is abutted against the insertion portion or the insertion auxiliary member to reduce resistance when the insertion portion or the insertion auxiliary member is inserted and removed.

In a twenty-fifth aspect of the invention according to the twenty-second or the twenty-fourth aspect, the holding device further comprises an urging force adjustment device which adjusts an urging force of the urging device. Thus, according to the twenty-fifth aspect, the urging force can be adjusted to ensure abutment and movement of the roller also when an insertion portion and/or an insertion auxiliary member having a different diameter is used.

In a twenty-sixth aspect of the invention according to any one of the twenty-first to the twenty-fifth aspects, the holding device further comprises a lock device which locks the roller at a stop of the motor. According to the twenty-sixth aspect, even if an external force is applied to the endoscope or the insertion auxiliary member at a stop of the motor, the roller is not rotated and the insertion portion or the insertion auxiliary member is not moved.

According to the holding device, the endoscopic device, and the operating method of the endoscopic device of the invention, the endoscope and/or the insertion auxiliary member is held by the holding device to improve operability, allow an operation by an operator by himself/herself, and facilitate automation.

BRIEF DESCRIPTION OF THE DRAWINGS

FIGS. 14A and 14B are sectional views of a holding device having a handle;

DETAILED DESCRIPTION OF THE PREFERRED EMBODIMENTS

Figure 1:
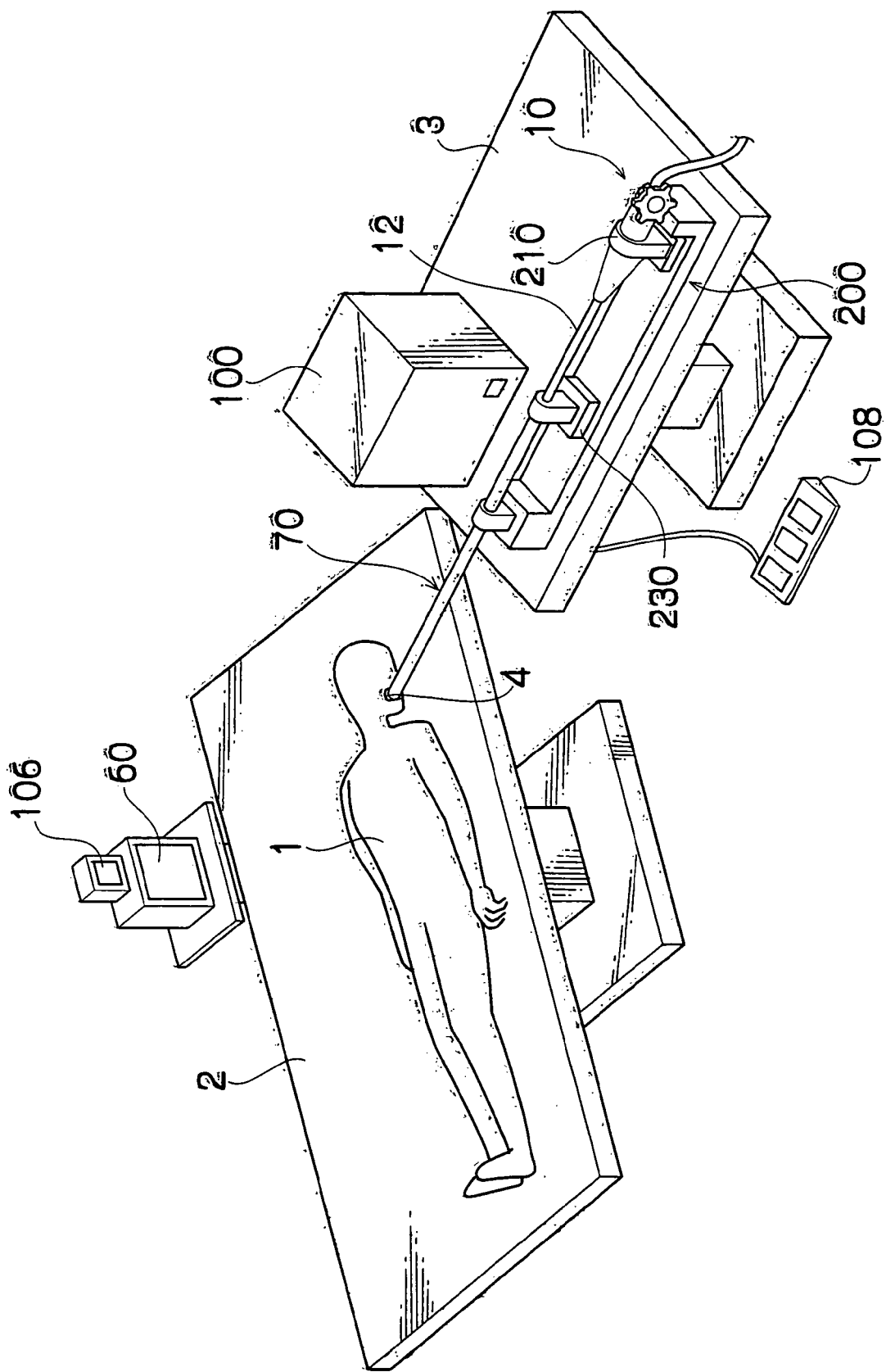
FIG. 1 is a perspective view of an inside of an examination room to which an endoscopic device according to the invention is applied.

Now, a preferred embodiment of a holding device, an endoscopic device, and an operating method of the endoscopic device according to the invention will be described with reference to the accompanying drawings. FIG. 1 is a perspective view of an inside of an examination room to which the holding device and the endoscopic device according to the invention are applied. As shown in FIG. 1, an examination table 2 on which a patient 1 lies is provided in the examination room. An operator (not shown) stands in front of the examination table 2 for operation. A below described monitor 60 and a balloon monitor 106 are provided at the back of the examination table 2.

An auxiliary table 3 is placed adjacent to the examination table 2 in front of the examination table 2. A below described holding device 200 is provided on the auxiliary table 3, and an endoscope 10 and an insertion auxiliary member 70 are held by the holding device 200. A light source device 20, a processor 30, a balloon control device 100 or the like described below may be provided on the auxiliary table 3. Instead of providing the auxiliary table 3, the holding device 200 may be provided on an examination table 2 having a space for the auxiliary table 3.

Figure 2:
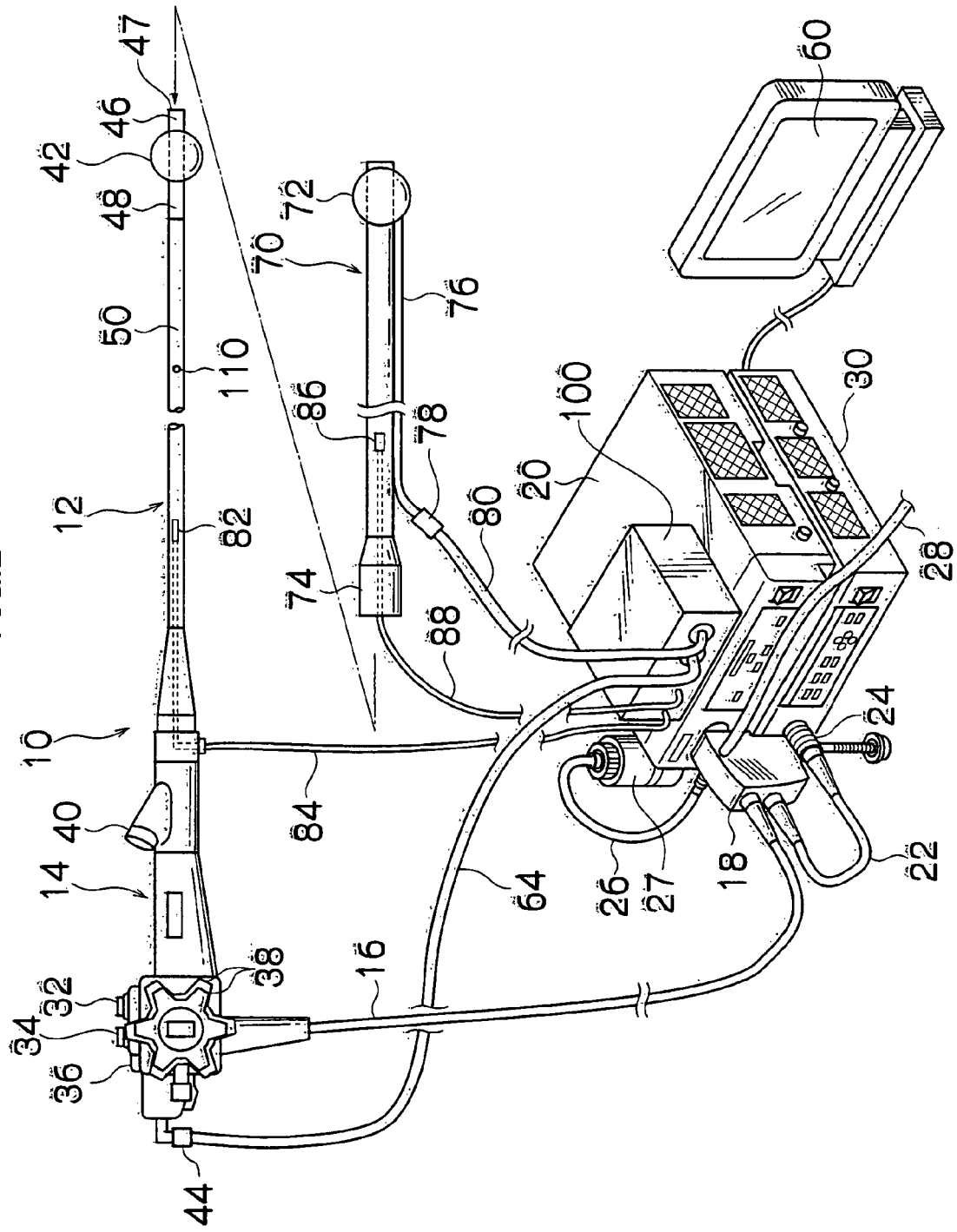
FIG. 2 shows a system configuration of an embodiment of the endoscopic device according to the invention.

FIG. 2 shows a system configuration of an embodiment of the endoscopic device according to the invention. The endoscopic device according to the embodiment mainly includes the endoscope 10, the light source device 20, the processor 30, an insertion auxiliary member 70, the balloon control device 100, and the below described holding device 200 in FIG. 4.

As shown in FIG. 2, the endoscope 10 includes an insertion portion 12 to be inserted into a body cavity, and a hand operation portion 14 connected to the insertion portion 12. A universal cable 16 is connected to the hand operation portion 14, and an LG (Light Guide) connector 18 is provided at a tip of the universal cable 16. The LG connector 18 is removably connected to the light source device 20 to allow illumination light to be transmitted to a below described illumination optical system 54 (see FIG. 3) at a tip of the insertion portion 12. An electric connector 24 is connected to the LG connector 18 via a cable 22, and the electric connector 24 is removably connected to the processor 30. The LG connector 18 is connected to a water storage tank 27 via an air/water feed tube 26, and water is fed from the water storage tank 27 via the tube 26. The LG connector 18 is connected to an unshown suction device via a suction tube 28, and air is sucked from the tip of the insertion portion 12 via the suction tube 28.

The insertion portion 12 includes a tip portion 46, a bending portion 48, and a soft portion 50, and the bending portion 48 is remotely bent by rotating a pair of angle knobs 38 and 38 provided on the hand operation portion 14. This allows a tip surface 47 of the tip portion 46 to be directed to a desired direction.

Figure 3:
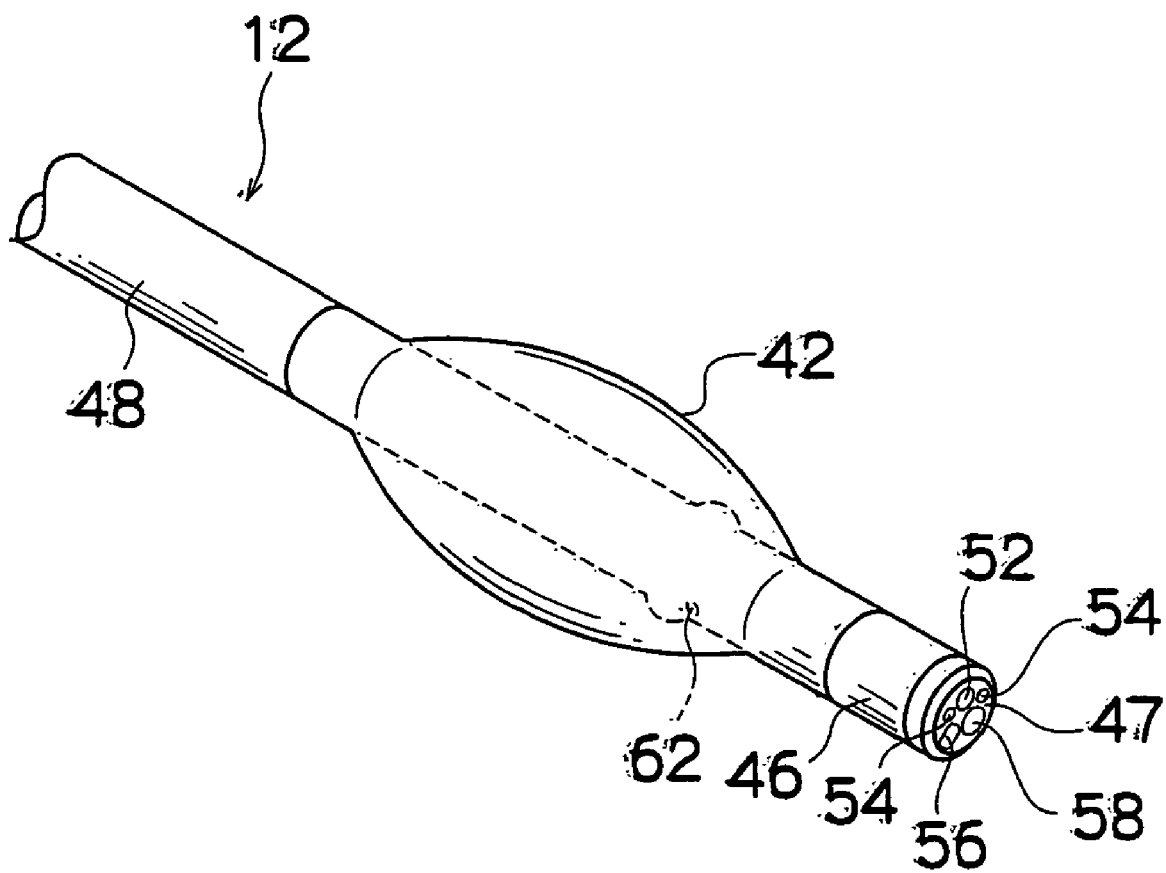
FIG. 3 is a perspective view of a tip of an insertion portion in FIG. 2.

As shown in FIG. 3, an observation optical system 52, illumination optical systems 54, an air/water feed nozzle 56, and a forceps opening 58 are provided in the tip surface 47 of the tip portion 46. A CCD (not shown) is provided behind the observation optical system 52, and a signal cable is connected to a substrate that supports the CCD. The signal cable is inserted through the insertion portion 12, the hand operation portion 14, and the universal cable 16, extended to the electric connector 24, and connected to the processor 30 in FIG. 2. Thus, an observation image captured by the observation optical system 52 is formed on a light receiving surface of the CCD and converted into an electric signal. Then, the electric signal is output to the processor 30 via the signal cable, and converted into a video signal. This causes an observation image to be displayed on the monitor 60 connected to the processor 30.

An emission end of a light guide (not shown) is provided behind the illumination optical systems 54 in FIG. 3. This light guide is inserted through the insertion portion 12, the hand operation portion 14, and the universal cable 16 in FIG. 2, and an incident end of the light guide is provided in the LG connector 18. Thus, the LG connector 18 is connected to the light source device 20 to cause the illumination light from the light source device 20 to be transmitted to the illumination optical systems 54 via the light guide and emitted forward from the illumination optical systems 54.

The air/water feed nozzle 56 in FIG. 3 communicates with a valve (not shown) operated by an air/water feed button 32 in FIG. 2. The valve is connected to the tank 27 via the air/water feed tube 26, and connected to an air pump (not shown) in the light source device 20. Then, the air/water feed button 32 is operated to feed air fed from the air pump or water fed from the tank 27 to the air/water feed nozzle 56. This allows air or water to be jetted from the air/water feed nozzle 56 toward the observation optical system 52 at the tip of the insertion portion 12.

The forceps opening 58 in FIG. 3 communicates with a forceps insertion portion 40 in FIG. 2. Thus, a treatment tool is inserted through the forceps insertion portion 40 to lead the treatment tool out of the forceps opening 58. The forceps opening 58 communicates with a valve (not shown) operated by a suction button 34, and the valve communicates with the suction tube 28. Therefore, the suction device connected to a tip of the suction tube 28 is driven to allow a lesion area or the like to be sucked from the forceps opening 58.

As shown in FIG. 3, a first balloon 42 made of an elastic body such as rubber is fitted to an outer peripheral surface at the tip of the insertion portion 12. The first balloon 42 is formed into a substantially cylindrical shape with narrowed opposite ends. The first balloon 42 is fitted in such a manner that the insertion portion 12 is inserted through the first balloon 42 and placed in a desired position, and then the opposite ends of the first balloon 42 are secured to the insertion portion 12.

An air vent 62 is formed in the outer peripheral surface of the insertion portion 12 to which the first balloon 42 is fitted. The air vent 62 communicates with a supply/suction port 44 in FIG. 2 via an unshown tube. A tube 64 is connected to the supply/suction port 44 and the balloon control device 100. The balloon control device 100 is a device which supplies and sucks air into and from the first balloon 42 via the tube 64, and controls air pressure at that time. The first balloon 42 expands into a substantially spherical shape by air being supplied thereinto or sticks to the outer peripheral surface of the insertion portion 12 by air being sucked therefrom.

On the other hand, the insertion auxiliary member 70 in FIG. 2 is formed into a cylindrical shape, has an inner diameter slightly larger than an outer diameter of the insertion portion 12, and has sufficient flexibility. A hard grip 74 is provided at a base end of the insertion auxiliary member 70, and the insertion portion 12 is inserted through the grip 74. A second balloon 72 made of latex is fitted to a tip of the insertion auxiliary member 70. The second balloon 72 is formed into a substantially cylindrical shape with narrowed opposite ends, and fitted with the insertion auxiliary member 70 being passed therethrough. A tube 76 stuck to an outer peripheral surface of the insertion auxiliary member 70 communicates with the second balloon 72. A connector 78 is provided at an end of the tube 76, and a tube 80 is removably connected to the connector 78. The tube 80 is connected to the balloon control device 100, and the balloon control device 100 supplies and sucks air into and from the tube 80, and controls air pressure at that time. Thus, the balloon control device 100 is driven to allow air to be supplied into and sucked from the second balloon 72. The second balloon 72 expands into a substantially spherical shape by air being supplied thereinto or sticks to an outer peripheral surface of the insertion auxiliary member 70 by air being sucked therefrom.

As shown in FIG. 2, a strain gauge 82 that measures the amount of extension of the soft portion 50 of the insertion portion 12 is provided at a predetermined position in the insertion portion 12, and the strain gauge 82 measures the amount of extension of the soft portion 50 when the insertion portion 12 is inserted or withdrawn. A signal line 84 is connected to the strain gauge 82, and the signal line 84 is inserted through the insertion portion 12, extended out of the hand operation portion 14, and then connected to the balloon control device 100. The balloon control device 100 controls to reduce the amount of extension of the soft portion 50 when an electrical resistance value of the strain gauge 82 exceeds a threshold value. For example, the below described holding device 200 is controlled to stop movement (that is, insertion or withdrawal) of the endoscope 10 or move the endoscope 10 in an opposite direction. An automatic injection device which automatically injects a lubricant between an inner peripheral surface of the insertion auxiliary member 70 and the outer peripheral surface of the insertion portion 12 may be provided to supply the lubricant depending on the measurement value of the strain gauge 82. This reduces frictional resistance between the insertion auxiliary member 70 and the insertion portion 12, thereby reducing loads. When the electrical resistance value of the strain gauge 82 exceeds the threshold value when the insertion portion 12 is withdrawn, a solenoid valve unit 144 (see FIG. 8) that communicates with the first balloon 42 may be caused to communicate with the outside to leak air from the first balloon 42. This allows the insertion portion 12 to be smoothly withdrawn to reduce the amount of extension of the soft portion 50, thereby reducing burdens on the patient.

A strain gauge 86 that measures the amount of extension of the insertion auxiliary member 70 is provided at a predetermined position in the insertion auxiliary member 70, and the strain gauge 86 measures the amount of extension of the insertion auxiliary member 70 when the insertion auxiliary member 70 is inserted or withdrawn. A signal line 88 is connected to the strain gauge 86, and the signal line 88 is inserted through the insertion auxiliary member 70, extended out of the grip 74, and then connected to the balloon control device 100. The balloon control device 100 controls to reduce the amount of extension of the insertion auxiliary member 70 when an electrical resistance value of the strain gauge 86 exceeds a threshold value. For example, the below described holding device 200 is controlled to stop movement (that is, insertion or withdrawal) of the insertion auxiliary member 70 or move the insertion auxiliary member 70 in an opposite direction. An automatic injection device of a lubricant may be provided to supply the lubricant depending on the measurement value of the strain gauge 86. When the electrical resistance value of the strain gauge 86 exceeds the threshold value when the insertion auxiliary member 70 is withdrawn, a solenoid valve unit 148 (see FIG. 8) that communicates with the second balloon 72 may be caused to communicate with the outside to leak air from the second balloon 72. This allows the insertion auxiliary member 70 to be smoothly withdrawn to reduce the amount of extension of the insertion auxiliary member 70, thereby reducing burdens on the patient.

Figure 4:
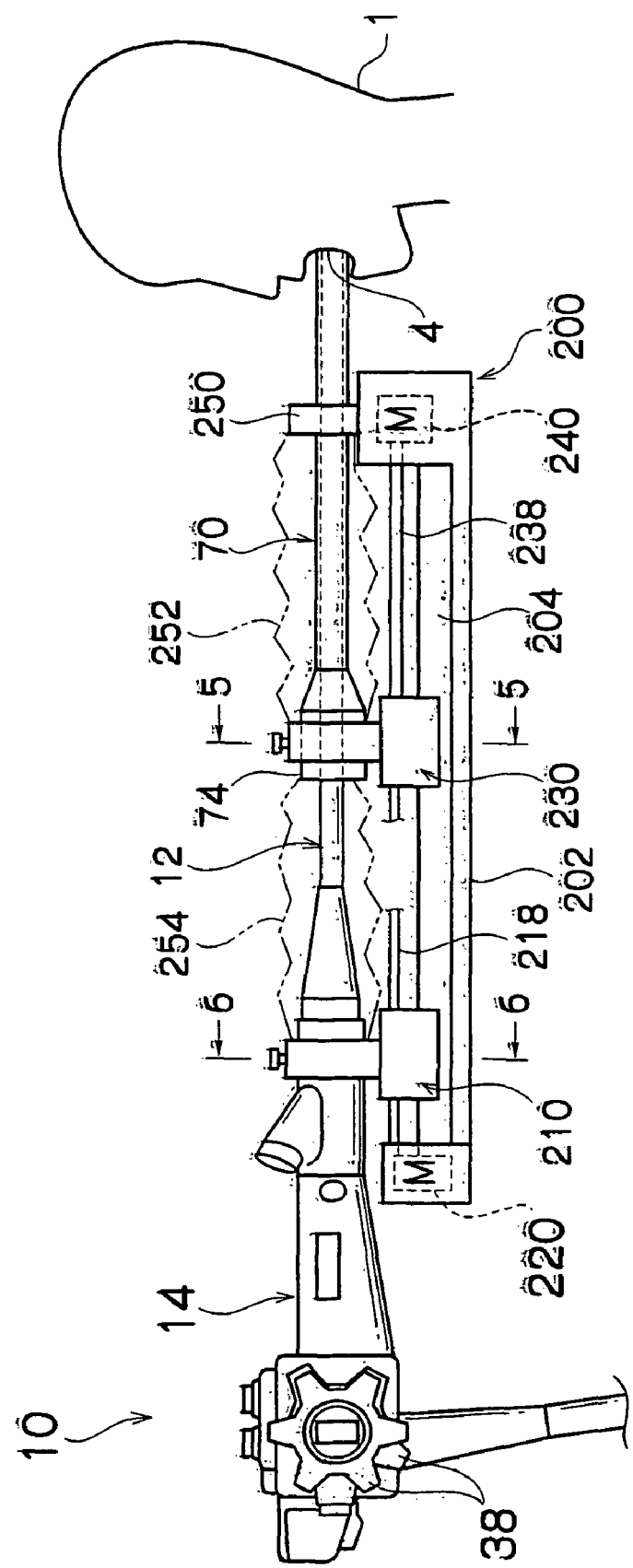
FIG. 4 is a side view of a configuration of a holding device in FIG. 1.
Figure 5:
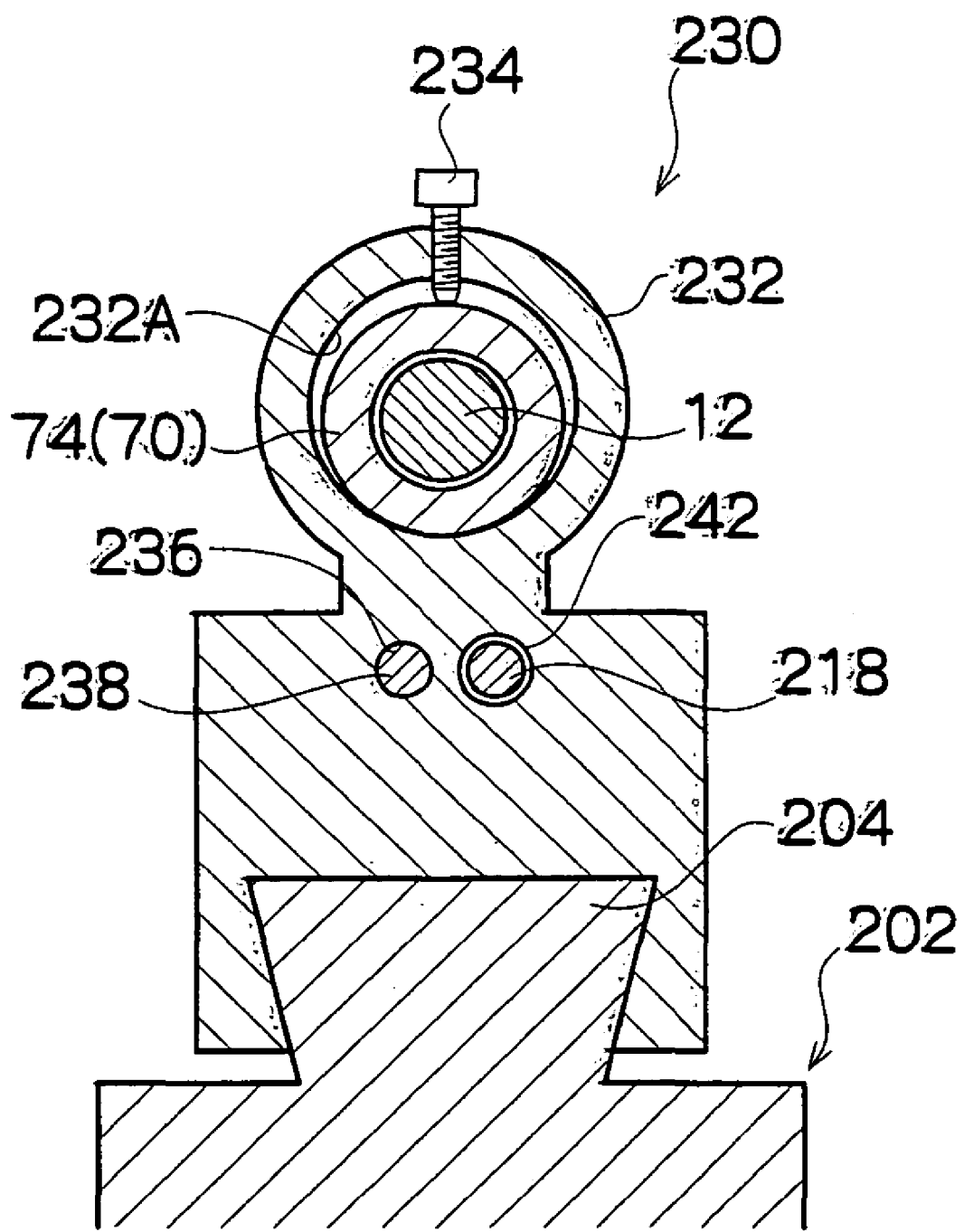
FIG. 5 is a sectional view taken along the line 5-5 in FIG. 4.
Figure 6:
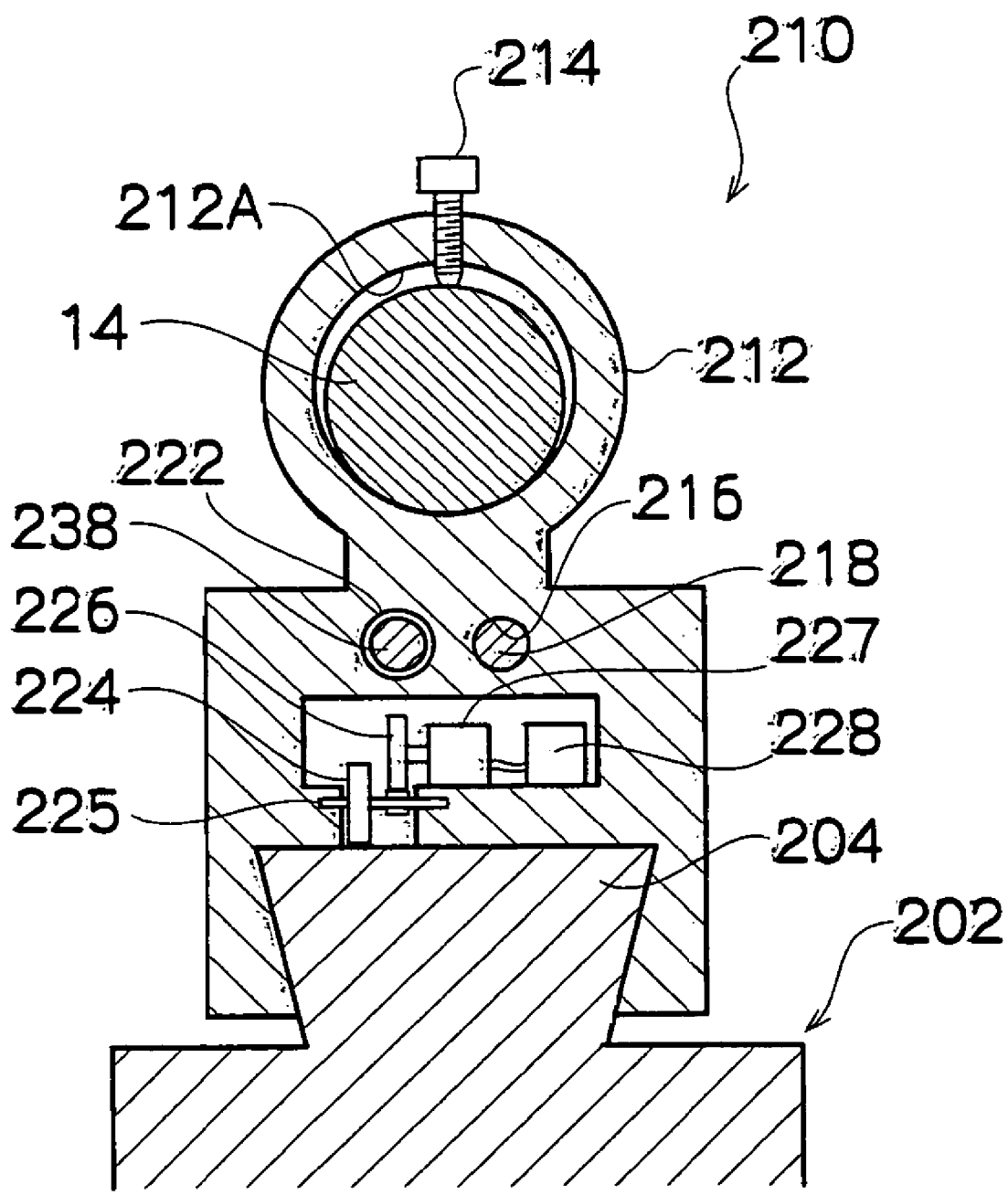
FIG. 6 is a sectional view taken along the line 6-6 in FIG. 4.

The endoscope 10 and the insertion auxiliary member 70 thus configured are held by the holding device 200 in FIG. 4. The holding device 200 has a stage 202, and a guide rail 204 is laid on the stage 202. The guide rail 204 is placed linearly toward the mouth 4 of the patient 1, and an endoscope holder 210 and an auxiliary member holder 230 are slidably supported along the guide rail 204. The guide rail 204 is formed into a dovetail as shown in FIGS. 5 and 6, and the endoscope holder 210 and the auxiliary member holder 230 have dovetail grooves, so that both engage each other. Thus, the endoscope holder 210 and the auxiliary member holder 230 can slide along the guide rail 204 without dropping off. The shape of engagement between the guide rail 204 and the endoscope holder 210 or the auxiliary member holder 230 is not limited as long as the holders are slidable.

As shown in FIG. 5, the auxiliary member holder 230 has a ring portion 232, and a through hole 232A having an inner diameter slightly larger than an outer diameter of the grip 74 of the insertion auxiliary member 70 is formed in the ring portion 232. A securing screw 234 is threaded into the ring portion 232 from an outer peripheral surface thereof, and the securing screw 234 is fastened to cause a tip of the securing screw 234 to protrude from an inner peripheral surface of the ring portion 232. Thus, the grip 74 of the insertion auxiliary member 70 is inserted into and placed in the through hole 232A of the ring portion 232, and then the securing screw 234 is fastened, thereby causing the tip of the securing screw 234 to engage the grip 74 and causing the insertion auxiliary member 70 to be held by the auxiliary member holder 230.

A screw hole 236 is formed in the auxiliary member holder 230, and a feed screw 238 is threaded into the screw hole 236. As shown in FIG. 4, the feed screw 238 is placed along the guide rail 204 and rotatably supported by the stage 202. A motor 240 that rotates the feed screw 238 is provided at a tip of the stage 202, and the feed screw 238 is rotated by the motor 240 to cause the auxiliary member holder 230 to slide along the guide rail 204. Specifically, the auxiliary member holder 230 is linearly moved with respect to the mouth 4 of the patient 1. This allows the insertion auxiliary member 70 held by the auxiliary member holder 230 to be linearly guided with respect to the mouth 4 of the patient 1.

A hole 242 through which a below described feed screw 218 is passed is also formed in the auxiliary member holder 230 in FIG. 5. The hole 242 is formed to be larger than an outer diameter of the feed screw 218.

On the other hand, as shown in FIG. 6, the endoscope holder 210 has a ring portion 212, and a through hole 212A into which the hand operation portion 14 can be inserted is formed in the ring portion 212. A securing screw 214 is threaded into the ring portion 212 from an outer peripheral surface thereof, and the securing screw 214 is fastened to cause a tip of the securing screw 214 to protrude from an inner peripheral surface of the ring portion 212. Thus, the hand operation portion 14 is inserted into the through hole 212A, and then the securing screw 214 is fastened, thereby causing the tip of the securing screw 214 to engage the hand operation portion 14 and causing the hand operation portion 14 to be secured to the endoscope holder 210.

A screw hole 216 is formed in the endoscope holder 210, and a feed screw 218 is threaded into the screw hole 216. As shown in FIG. 4, the feed screw 218 is placed along the guide rail 204 and rotatably supported by the stage 202. A motor 220 that rotates the feed screw 218 is provided at an end of the stage 202, and the feed screw 218 is rotated by the motor 220 to cause the endoscope holder 210 to slide along the guide rail 204. Specifically, the endoscope holder 210 is linearly moved with respect to the mouth 4 of the patient 1. This allows the insertion portion 12 of the endoscope 10 held by the endoscope holder 210 to be linearly guided with respect to the mouth 4 of the patient 1.

A hole 222 through which the above described feed screw 238 for the auxiliary member holder 230 is passed is also formed in the endoscope holder 210 in FIG. 6. The hole 222 is formed to be larger than an outer diameter of the feed screw 238.

Further, a roller 224 is rotatably supported in the endoscope holder 210 as an insertion length measurement device. The roller 224 is provided so as to protrude toward the guide rail 204, and abuts against the guide rail 204 and is rotated when the endoscope holder 210 is slid along the guide rail 204.

A gear 226 is connected to a rotation axis 225 of the roller 224 so that torque of the roller 224 is transmitted to the gear 226. The gear 226 is connected to a sensor 227 via an unshown one-way clutch, and the RPM of the gear 226 only in one direction is detected by the sensor 227. The rotational direction to be detected is a direction of rotation of the gear 226 when the endoscope holder 210 is advanced toward the mouth 4 of the patient 1.

A calculation device 228 is connected to the sensor 227, and the calculation device 228 converts the RPM of the gear 226 detected by the sensor 227 into an insertion length of the insertion portion 12. Then, conversion values are summed to obtain the total insertion length. The calculation device 228 is connected to the balloon control device 100 so that the total insertion length obtained by the calculation device 228 is displayed on the balloon monitor 106 or the like of the balloon control device 100. This allows the operator to recognize which position in a body cavity the tip of the insertion portion 12 reach.

As shown in FIG. 4, a guide ring 250 is provided at an end of the tip of the stage 202. The guide ring 250 has an inner diameter slightly larger than the outer diameter of the insertion auxiliary member 70 so that the insertion auxiliary member 70 can be inserted into the guide ring 250 and guided.

A cover 252 shown by the dash-double dot lines is provided between the guide ring 250 and the auxiliary member holder 230. The cover 252 is formed into an extendable cylindrical shape (for example, bellows) and attached so as to surround the insertion auxiliary member 70. Opposite ends of the cover 252 are detachably connected to the guide ring 250 and the auxiliary member holder 230 so that the cover 252 can be detached and cleaned as required. The insertion auxiliary member 70 is surrounded by the cover 252 thus configured to prevent a splash of a body fluid sticking to the outer surface of the insertion auxiliary member 70. This allows the operator to operate without making his/her hands dirty.

A cover 254 shown by the dash-double dot lines is provided between the auxiliary member holder 230 and the endoscope holder 210. Like the cover 252, the cover 254 is formed into an extendable cylindrical shape (for example, bellows) and attached so as to surround the insertion portion 12. Opposite ends of the cover 254 are detachably connected to the auxiliary member holder 230 and the endoscope holder 210 so that the cover 254 can be detached and cleaned as required. The insertion portion 12 is surrounded by the cover 254 thus configured to prevent a splash of a body fluid sticking to the outer surface of the insertion portion 12. This allows the operator to operate without making his/her hands dirty.

Figure 7:
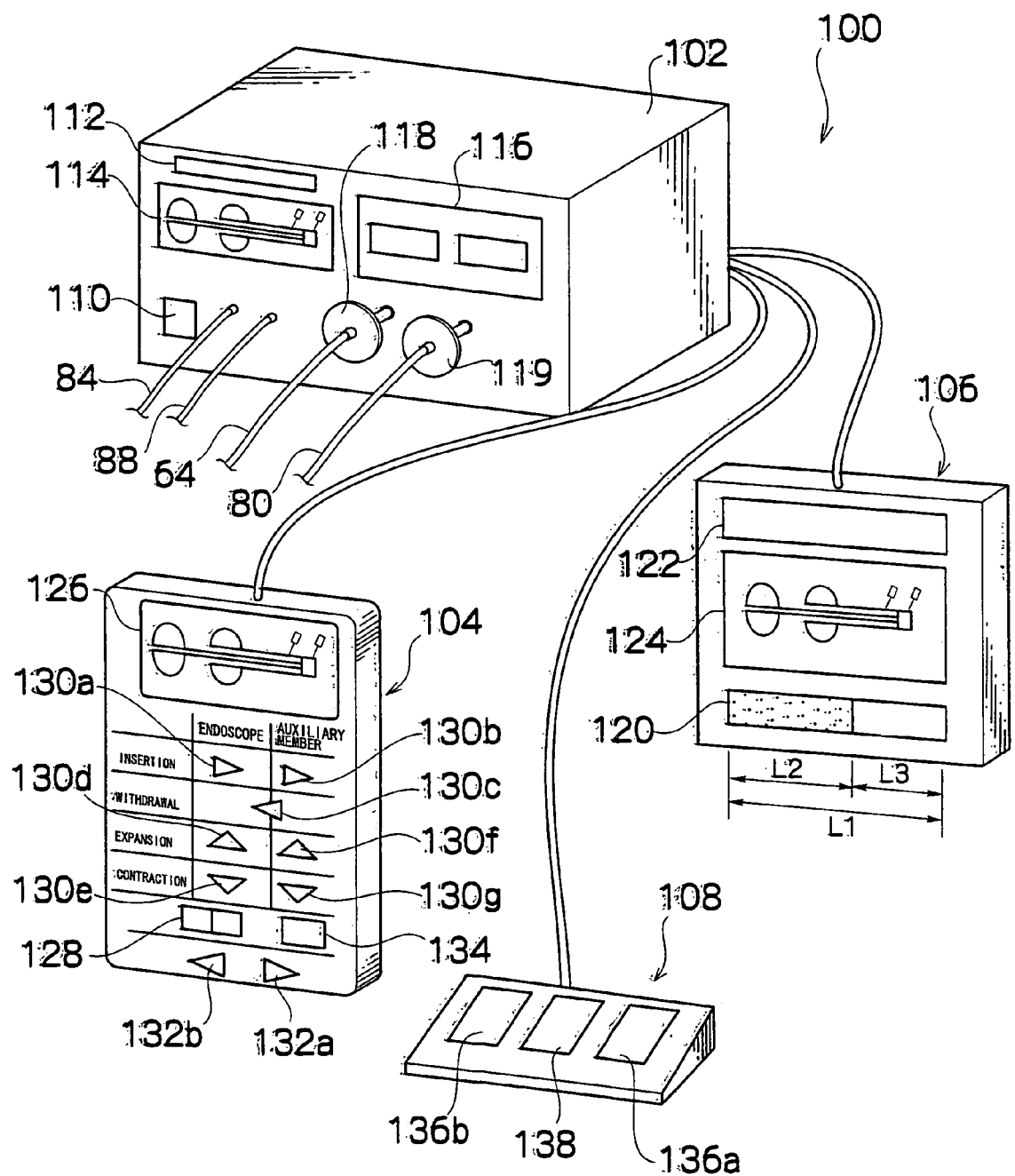
FIG. 7 is a perspective view of a configuration of a balloon control device.

FIG. 7 is a perspective view of the balloon control device 100. As shown in FIG. 7, the balloon control device 100 mainly includes a device body 102, a remote controller 104, the balloon monitor 106, and a foot switch 108. A power switch 110, an error display portion 112, a state display portion 114, a pressure value display portion 116, and gas/liquid separation filters 118 and 119 are provided on a front panel of the device body 102, and the above described tubes 64 and 80 are connected to the gas/liquid separation filters 118 and 119. A liquid sucked via the tubes 64 and 80 is subjected to gas/liquid separation by the gas/liquid separation filters 118 and 119 and removed. This prevents the liquid from being sucked into the device body 102.

Letters or numerals indicating a break in the first balloon 42 or the second balloon 72 if any are displayed on the error display portion 112. An expansion state of the first balloon 42 or the second balloon 72 is displayed on the state display portion 114. Internal pressure of the first balloon 42 and internal pressure of the second balloon 72 measured by below described pressure sensors 146 and 150 (see FIG. 8) are displayed on the pressure value display portion 116.

The balloon monitor 106 is mounted to the monitor 60 as shown in FIG. 1 so that the operator can observe the balloon monitor 106 together with a screen of the monitor 60. The balloon monitor 106 in FIG. 7 has an error display portion 122 and a state display portion 124 that display in the same manner as the error display portion 112 and the state display portion 114. Thus, the expansion state and occurrence of errors of the first balloon 42 or the second balloon 72 can be also recognized by observing the balloon monitor 106. The balloon monitor 106 also has a total insertion length display portion 120. In the total insertion length display portion 120, L2 indicating the total insertion length lights up with respect to L1 indicating the entire length of intestine so that a glance at the total insertion length display portion 120 shows L3 indicating the remaining distance of the intestine. A display portion like the total insertion length display portion 120 may be provided on the front panel of the device body 102 or the remote controller 104.

The remote controller 104 has a state display portion 126 that displays in the same manner as the state display portion 114. The remote controller 104 also has a mode selection switch 128 that switches between a manual mode and an automatic mode, operation buttons 130a to 130g that become operative in the manual mode, operation buttons 132a and 132b that become operative in the automatic mode, and a stop button 134 that is common to both modes.

When the operation button 130a for the manual mode is pressed, the motor 220 in FIG. 4 is driven to advance the endoscope holder 210 a predetermined distance. Likewise, when the operation button 130b in FIG. 7 is pressed, the auxiliary member holder 230 in FIG. 4 is advanced a predetermined distance. When the operation button 130c in FIG. 7 is pressed, the endoscope holder 210 and the auxiliary member holder 230 in FIG. 4 are simultaneously retracted.

When the operation button 130d in FIG. 7 is pressed, air is fed into the first balloon 42 in FIG. 2, and when the operation button 130e in FIG. 7 is pressed, air is sucked from the first balloon 42 in FIG. 2. Likewise, when the operation button 130f in FIG. 7 is pressed, air is fed into the second balloon 72 in FIG. 2, and when the operation button 130g in FIG. 7 is pressed, air is sucked from the second balloon 72 in FIG. 2.

On the other hand, each press of the operation button 132a for the automatic mode causes the operation to move to a next operation (step). Then, a press of the operation button 132b causes the operation to return to a former operation.

The remote controller 104 has the state display portion 126 only, but may have an error display portion, a total insertion length display portion, a pressure value display portion, or the like. A mode display portion that displays a present mode may be provided.

The foot switch 108 in FIG. 7 has operation buttons 136a and 136b for the automatic mode and a stop button 138. The operation buttons 136a and 136b have the same function as the operation buttons 132a and 132b of the remote controller 104. The foot switch 108 is placed below the auxiliary table 2 as shown in FIG. 1. This allows the operator to advance the operation by foot in the automatic mode. In the manual mode, the foot switch 108 may be pressed to adjust a flow rate of air supplied into and sucked from the first balloon 42 or the second balloon 72.

Figure 8:
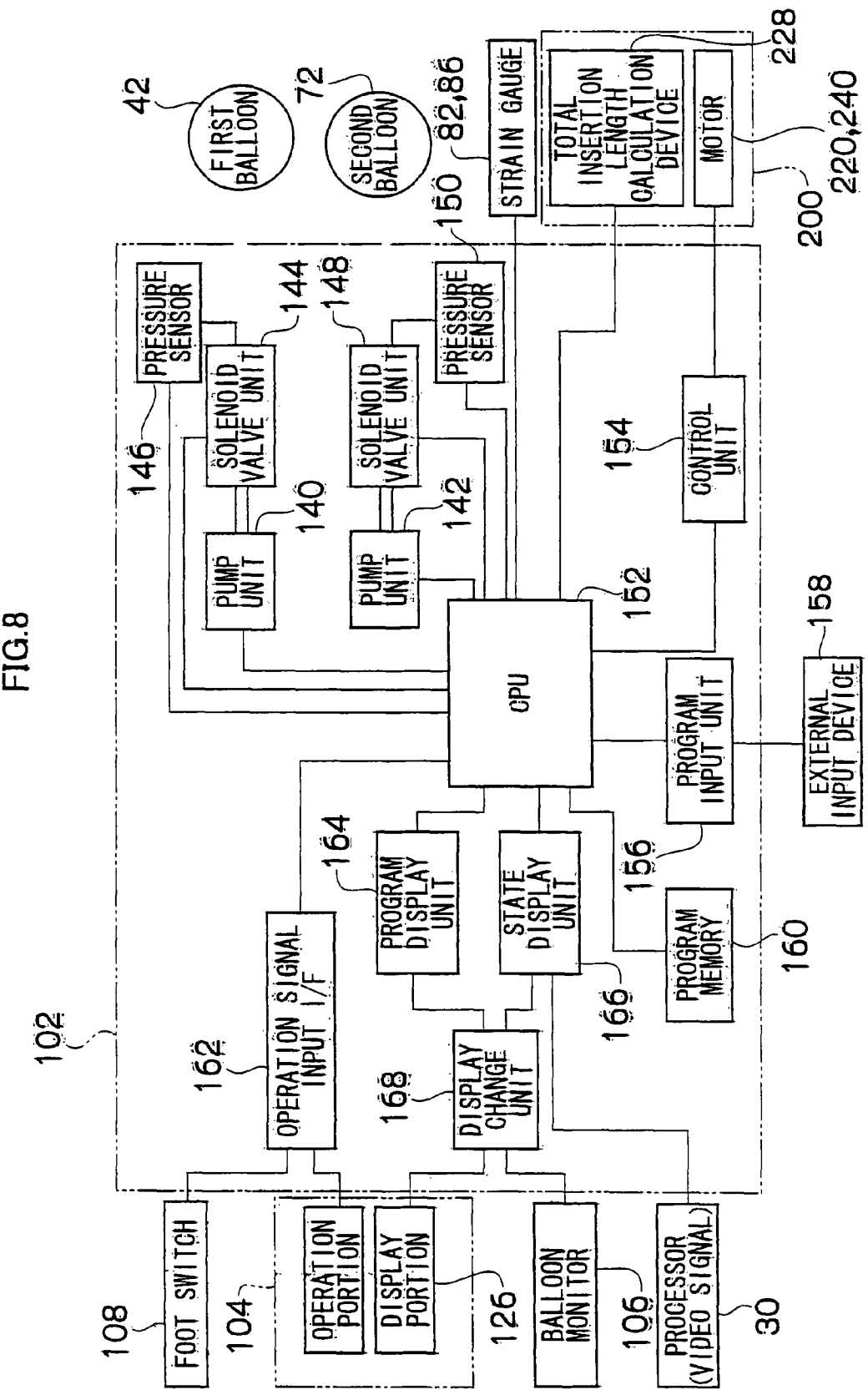
FIG. 8 is a block diagram of an internal configuration of the balloon control device.

FIG. 8 is a block diagram of an internal configuration of the balloon control device 100. As shown in FIG. 8, pump units 140 and 142 are provided in the device body 102. The pump unit 140 communicates with the first balloon 42 and the pressure sensor 146 via the solenoid valve unit 144, and the pump unit 142 communicates with the second balloon 72 and the pressure sensor 150 via the solenoid valve unit 148. The pump units 140 and 142 each have a pressure pump and a pressure reducing pump that are not shown, and the solenoid valve units 144 and 148 are switched so that one of the pressure pump and the pressure reducing pump communicates with the balloon. The pump units 140 and 142 and the solenoid valve units 144 and 148 are connected to a CPU 152, and the CPU 152 controls expansion of the first balloon 42 and the second balloon 72. Specifically, air is supplied from the pump unit 140 to expand the first balloon 42 and air is sucked by the pump unit 140 to contract the first balloon 42, or air is supplied from the pump unit 142 to expand the second balloon 72 and air is sucked by the pump unit 142 to contract the second balloon 72. At this time, the pump units 140 and 142 and the solenoid valve units 144 and 148 are controlled depending on the measurement values of the pressure sensors 146 and 150. This allows the first balloon 42 and the second balloon 72 to be controlled to predetermined internal pressures. When an error (for example, a break in the first balloon 42 or the second balloon 72) occurs, the error can be detected by the measurement values of the pressure sensors 146 and 150 to stop feeding or suction of air.

The strain gauges 82 and 86 are connected to the CPU 152, and when the measurement values of the strain gauges 82 and 86 exceed threshold values, the solenoid valve units 144 and 148 are controlled. Then, air is leaked from the first balloon 42 and the second balloon 72 to contract the first balloon 42 and the second balloon 72.

A control unit 154 for the holding device 200 is also connected to the CPU 152, and drive control of the motors 220 and 240 of the holding device 200 is performed via the control unit 154. Further, the CPU 152 is connected to the calculation device 228 of the holding device 200, and determines whether the insertion of the insertion portion 12 is to be continued (that is, whether the motors 220 and 240 are to be driven) based on the total insertion length obtained by the calculation device 228.

A program input unit 156 is connected to the CPU 152 so that a program can be input from an external input device 158 such as a keyboard. The input program is stored in a program memory 160. The program is a program of operation procedures performed in the automatic mode, and supply pressure and suction pressure of air into and from the first balloon 42 or the second balloon 72 are also set.

An operation signal input I/F 162 is connected to the CPU 152 so that operation signals are input from the foot switch 108 and operation portions of the remote controller 104 (that is, the mode selection switch 128, the operation buttons 130a to 130g, the operation buttons 132a and 132b, and the stop button 134). The CPU 152 outputs control signals to the pump units 140 and 142, the solenoid valve units 144 and 148, and the control unit 154 depending on the operation signals.

A program display unit 164 and a state display unit 166 are also connected to the CPU 152. The program display unit 164 and the state display unit 166 are connected to the balloon monitor 106 and the state display portion 126 of the remote controller 104 via a display change unit 168. Thus, the expansion states of the first balloon 42 and the second balloon 72 and also the program may be displayed on the balloon monitor 106 and the remote controller 104.

Figure 9:
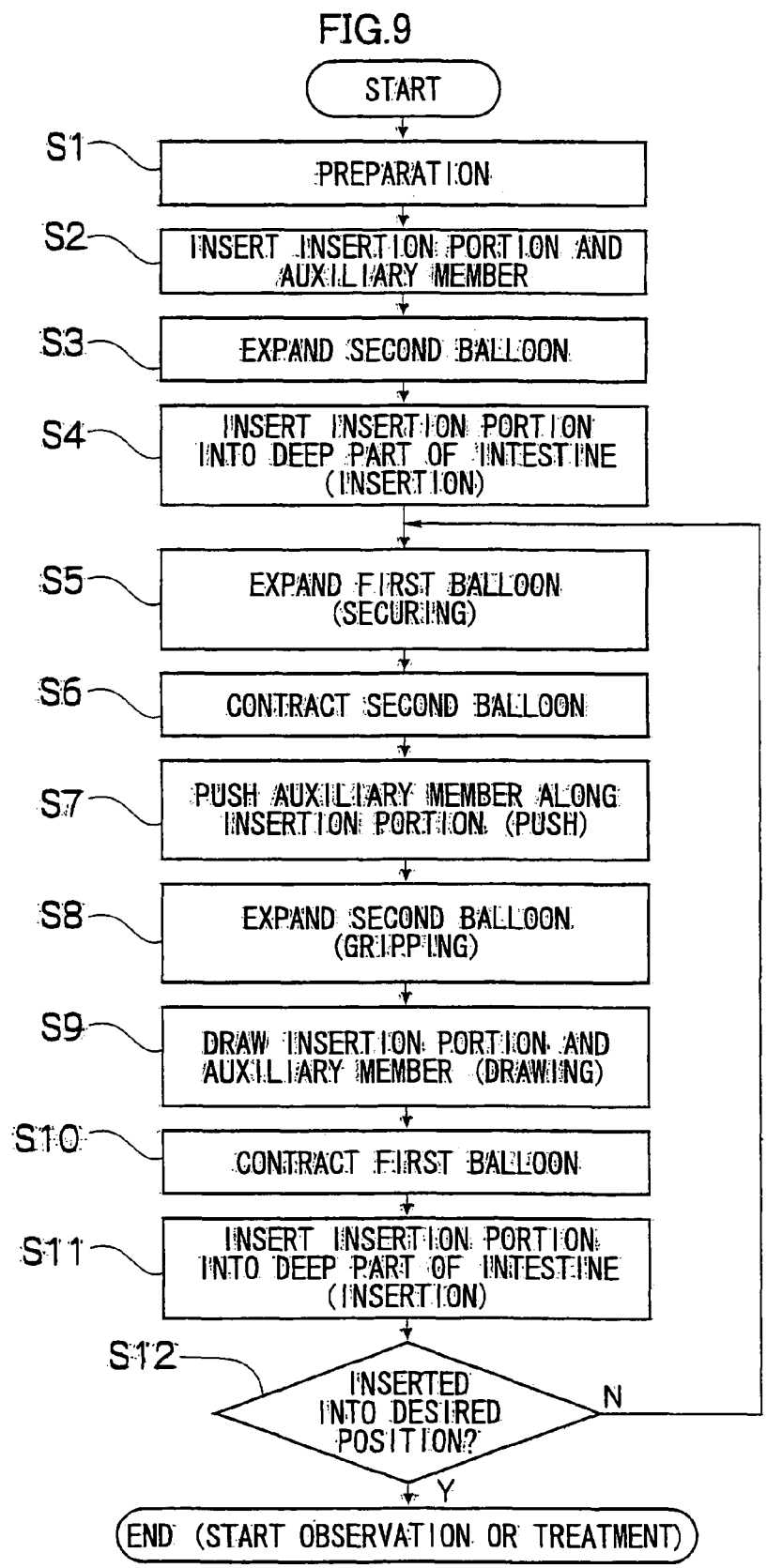
FIG. 9 is a flowchart of operation procedures of the endoscopic device according to the invention.

Next, an operating method of the endoscopic device thus configured will be described with reference to FIGS. 9 and 10A to 10H. FIG. 9 is a flowchart of the operation procedures of the endoscopic device, and FIGS. 10A to 10H illustrate the operation procedures of the endoscopic device.

First, as a preparation for insertion, the insertion auxiliary member 70 is placed over the insertion portion 12, the hand operation portion 14 of the endoscope 10 is secured to the endoscope holder 210, and the insertion auxiliary member 70 is secured to the auxiliary member holder 230 (Step S1). At this time, the first balloon 42 and the second balloon 72 are contracted.

One of the automatic mode and the manual mode is selected by the mode selection switch 128 of the remote controller 104 in FIG. 7 to perform operations hereinafter. The case where the automatic mode is selected will be first described. When the automatic mode is selected, the operation button 132a of the remote controller 104 or the operation button 136a of the foot switch 108 (hereinafter collectively referred to as an advance button) is pressed to cause operation steps to automatically advance.

Figure 10:
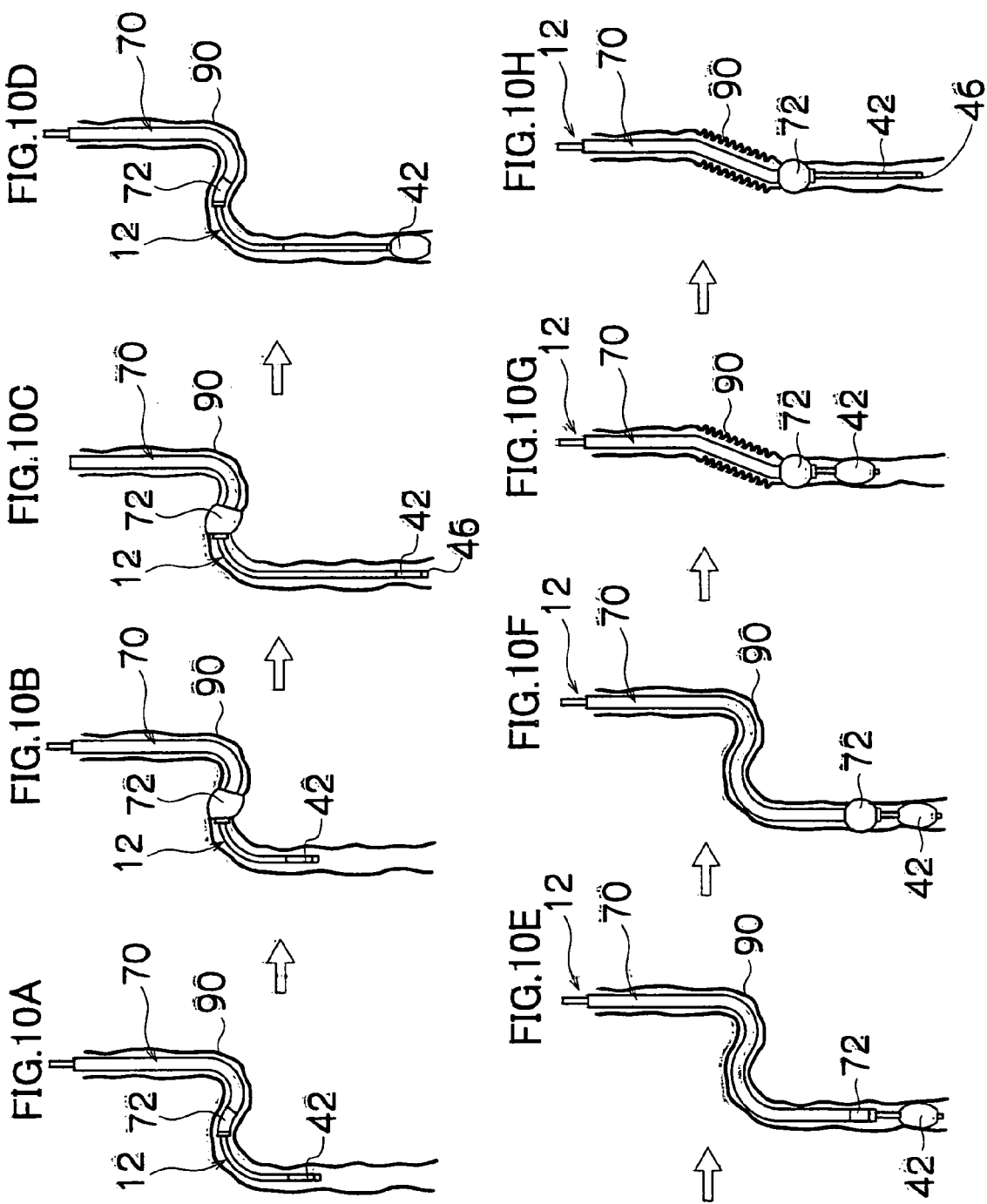
FIGS. 10A to 10H illustrate the operation procedures of the endoscopic device according to the invention.

For example, when the advance button is pressed after the preparation, the motors 220 and 240 in FIG. 4 are driven, and the endoscope holder 210 and the auxiliary member holder 230 are advanced a predetermined distance toward the mouth 4 of the patient 1 and then stopped. This causes the insertion portion 12 and the insertion auxiliary member 70 to be inserted into the body cavity (Step S2), and the tip of the insertion auxiliary member 70 reaches a bending portion in intestine 90 as shown in FIG. 10A.

When the advance button is next pressed, the pump unit 142 and the solenoid valve unit 148 in FIG. 8 are controlled to feed air into the second balloon 72. Then, air is fed into the second balloon 72 until the measurement value of the pressure sensor 150 reaches a predetermined range. This causes expansion of the second balloon 72 (Step S3), and the insertion auxiliary member 70 is secured to the intestine 90 via the second balloon 72 as shown in FIG. 10B.

When the advance button is pressed in this state, the motor 220 in FIG. 4 is driven, the endoscope holder 210 is advanced a predetermined distance toward the mouth 4 of the patient 1 and then stopped. At this time, the operator operates the angle knobs 38 and 38 on the hand operation portion 14 to bend the bending portion 48 of the insertion portion 12 (see FIG. 2) so as to follow the bending shape of the intestine 90. This causes the insertion portion 12 to be inserted into the intestine 90 (Step S4), and as shown in FIG. 10C, the tip of the insertion portion 12 is inserted into a deep part of the intestine 90. When the insertion portion 12 is inserted, the insertion length of the insertion portion 12 is measured by the insertion length measurement device constituted by the roller 224, the gear 226, and the sensor 227, and the measurement values are summed by the calculation device 228 to obtain the total insertion length.

When the advance button is next pressed, the pump unit 140 and the solenoid valve unit 144 in FIG. 8 are controlled to feed air into the first balloon 42. Then, air is fed into the first balloon 42 until the measurement value of the pressure sensor 146 reaches a predetermined range. This causes expansion of the first balloon 42 (Step S5), and the insertion portion 12 is secured to the intestine 90 via the first balloon 42 as shown in FIG. 10D.

When the advance button is pressed in this state, the pump unit 142 and the solenoid valve unit 148 in FIG. 8 are controlled to suck air from the second balloon 72. Then, air is sucked from the second balloon 72 until the measurement value of the pressure sensor 150 reaches a predetermined range. This causes contraction of the second balloon 72 (Step S6), and the second balloon 72 sticks to the surface of the insertion auxiliary member 70 as shown in FIG. 10D.

When the advance button is next pressed, the motor 240 in FIG. 4 is driven to move the auxiliary member holder 230 toward the mouth 4 of the patient 1. Thus, the insertion auxiliary member 70 is linearly guided and inserted into the patient 1, and the insertion auxiliary member 70 is pushed with the guide of the insertion portion 12 of the endoscope 10. The auxiliary member holder 230 is moved a predetermined distance and then stopped. This causes the insertion auxiliary member 70 to be inserted a predetermined distance (Step S7), and the second balloon 72 is placed immediately ahead of the first balloon 42 as shown in FIG. 10E. At this time, in the embodiment, the insertion length of the insertion auxiliary member 70 can be controlled by the drive control of the motor 240, thereby preventing the tip of the insertion auxiliary member 70 from coming into contact with the first balloon 42 of the insertion portion 12 and preventing damage to the first balloon 42.

When the advance button is pressed with the insertion auxiliary member 70 being inserted, the pump unit 142 and the solenoid valve unit 148 in FIG. 8 are controlled to feed air into the second balloon 72. Then, air is fed into the second balloon 72 until the measurement value of the pressure sensor 150 reaches a predetermined range. This causes expansion of the second balloon 72 (Step S8), and the insertion auxiliary member 70 is secured to the intestine 90 as shown in FIG. 10F. That is, the intestine 90 is gripped by the second balloon 72.

When the advance button is pressed in this state, the motors 220 and 240 in FIG. 4 are driven to simultaneously move the endoscope holder 210 and the auxiliary member holder 230 a predetermined distance in a retracting direction from the mouth 4 of the patient 1. This causes the insertion portion 12 and the insertion auxiliary member 70 to be simultaneously withdrawn from the mouth 4 of the patient 1, and the intestine 90 is gathered (Step S9). This causes contraction of the intestine 90 as shown in FIG. 10G to remove surplus bending or flection of the insertion auxiliary member 70. If the measurement values of the strain gauges 82 and 86 (see FIG. 2) exceed the threshold values when the intestine 90 is gathered, air is leaked from the first balloon 42 or the second balloon 72 to contract the first balloon 42 or the second balloon 72 by the balloon control device 100. This prevents a heavy load from being applied to the intestine 90.

When the advance button is pressed with the insertion portion 12 and the insertion auxiliary member 70 being drawn, the pump unit 140 and the solenoid valve unit 144 in FIG. 8 are controlled to suck air from the first balloon 42. Then, air is sucked from the first balloon 42 until the measurement value of the pressure sensor 146 reaches a predetermined range. This causes contraction of the first balloon 42 (Step S10), and the first balloon 42 sticks to the surface of the insertion portion 12 as shown in FIG. 10H.

When the advance button is next pressed, the motor 220 in FIG. 4 is driven, and the endoscope holder 210 is moved a predetermined distance toward the mouth 4 of the patient 1 and then stopped. This causes the insertion portion 12 to be inserted into a deep part of the intestine 90 (Step S11). At this time, the surplus bending or flection of the insertion auxiliary member 70 is removed to allow smooth insertion of the insertion portion 12.

When the insertion portion 12 is inserted into the deep part of the intestine 90, the balloon control device 100 determines whether the tip of the insertion portion 12 reaches a predetermined position, that is, whether the total insertion length obtained by the calculation device 228 in FIG. 6 reaches a set value (Step S12). When the set value is not reached, the above described operations (Step S5 to Step S11) are repeated. Specifically, the securing in FIG. 10D, the push in FIG. 10E, the gripping in FIG. 10F, the drawing in FIG. 10G, and the insertion in FIG. 10H are successively repeated. This allows the insertion portion 12 to be inserted to a deeper part of the intestine 90. Then, after the total insertion length reaches a desired value, observation or treatment by the endoscope 10 is performed.

According to the embodiment, the complex operations (Step S2 to Step S12) can be automatically performed simply by pressing the advance button. This eliminates the need for the operator to think of the operation procedures and facilitates the operation.

In the automatic mode, the operation button 132*b* of the remote controller 104 or the operation button 136*b* is operated to return to a former operation. The stop button 134 or 138 may be pressed to stop each operation.

In the embodiment, the manual mode may be selected by the mode selection switch 128 of the remote controller 104. When the manual mode is selected, any one of the operation buttons 130*a* to 130*g* is pressed at completion of each operation to perform a next operation. For example, in Step 2 to Step 11 described above, the operation buttons 130*a* and 130*b* are simultaneously pressed (Step S2), then the operation button 130*f* is pressed (Step S3), and further, the operation button 130*a* (Step S4), the operation button 130*d* (Step S5), the operation button 130*g* (Step S6), the operation button 130*b* (Step S7), the operation button 130*f* (Step S8), the operation button 130*c* (Step S9), the operation button 130*e* (Step S10), and the operation button 130*a* (Step S11) are successively pressed. The operation buttons 130*a* to 130*g* may be selectively successively pressed.

It is preferable that a light such as an LED is provided in each of the operation buttons 130*a* to 130*g* for the manual mode, each of the operation buttons 130*a* to 130*g* is configured so that lighting up of the light is clearly shown, and one of the operation buttons 130*a* to 130*b* in operation is lit up. This allows the operator to always recognize which operation is performed. One of the operation buttons 130*a* to 130*g* for a next operation may be lit in a different color to guide the next operation. Further, also in the automatic mode, the operation buttons 130*a* to 130*g* for the manual mode are lit to allow the operator to recognize the operation situation.

Next, an operation of the endoscopic device according to the invention will be described.

In the endoscopic device according to the embodiment, as shown in FIG. 4, the endoscope 10 and the insertion auxiliary member 70 are held by the holding device 200 and linearly guided with respect to the mouth 4 of the patient 1. Specifically, the endoscope 10 is held by the endoscope holder 210, the insertion auxiliary member 70 is held by the auxiliary member holder 230, and the endoscope holder 210 and the auxiliary member holder 230 are slidably supported along the guide rail 204 of the stage 202. This eliminates the need for gripping the endoscope 10 or the insertion auxiliary member 70, and allows the operator to concentrate on the operation of the hand operation portion 14 or the operation of the balloon control device 100. Also, there is no need for an assistant who operates the insertion auxiliary member 70 required for the conventional device, and this allows the operator to operate the endoscopic device by himself/herself.

According to the embodiment, the insertion portion 12 of the endoscope 10 and the insertion auxiliary member 70 each are linearly guided with respect to the mouth 4 of the patient 1 and inserted, thereby allowing insertion without applying an unnecessary force. This allows the insertion portion 12 and the insertion auxiliary member 70 to be smoothly inserted into the patient 1 to reduce burdens on the patient 1.

According to the embodiment, the endoscope holder 210 and the auxiliary member holder 230 are slid by driving the motors 240 and 240 to allow automatic insertion and removal of the insertion portion 12 and the insertion auxiliary member 70.

According to the embodiment, the strain gauges 82 and 86 that measure the withdrawal force are provided to prevent an excessive load from being applied, thereby preventing a heavy load from being applied to the intestine 90 to provide high safety.

In the embodiment, the insertion length of the insertion portion 12 is measured by the insertion length measurement device constituted by the roller 224, the gear 226, and the sensor 227 in FIG. 6, but the configuration of the insertion length measurement device is not limited to the embodiment. For example, a motor (for example, a stepping motor) capable of controlling the amount of rotation is used as the motor 220 to accurately control the amount of movement of the endoscope holder 210 and calculate the total insertion length.

Figure 11:
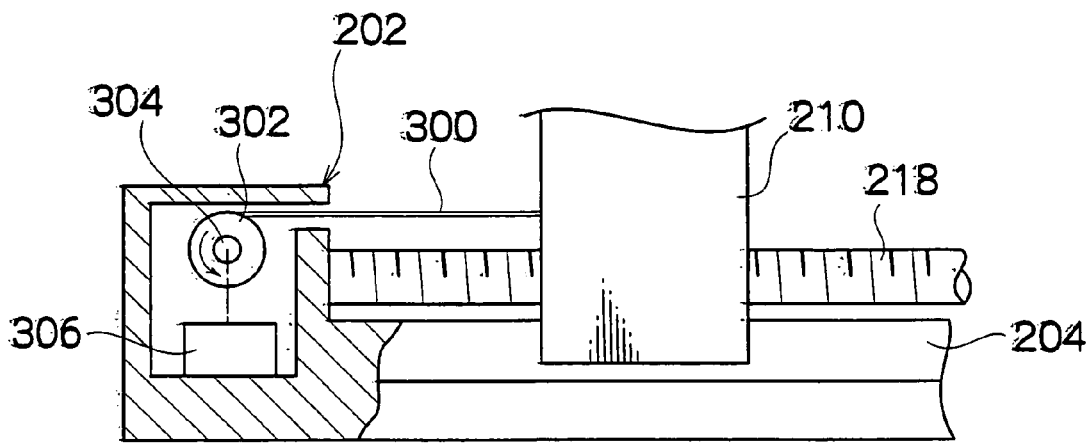
FIG. 11 is a side view of an insertion length measurement device having a different configuration from a configuration in FIG. 6.

As shown in FIG. 11, the insertion length may be measured by an insertion length measurement device constituted by a cord member 300, a winding roller 302, and a rotation amount sensor 304. The cord member 300 in FIG. 11 is connected at a tip thereof to the endoscope holder 210, and wound at a base end thereof by the winding roller 302. The winding roller 302 is mounted to the base end portion of the stage 202 (that is, an end opposite from the mouth 4 of the patient 1), and urged in the direction of arrow (a direction of winding the cord member 300) by an unshown urging device. This eliminates surplus flection of the cord member 300. The rotation amount sensor 304 is connected to the winding roller 302, and the rotation amount sensor 304 detects the amount of rotation when the cord member 300 is unreeled. Thus, a calculation device 306 converts the amount of rotation of the winding roller 302 into the amount of unreeling of the cord member 300 to calculate the insertion length of the insertion portion 12. Then, insertion lengths are summed to obtain the total insertion length.

Figure 12:
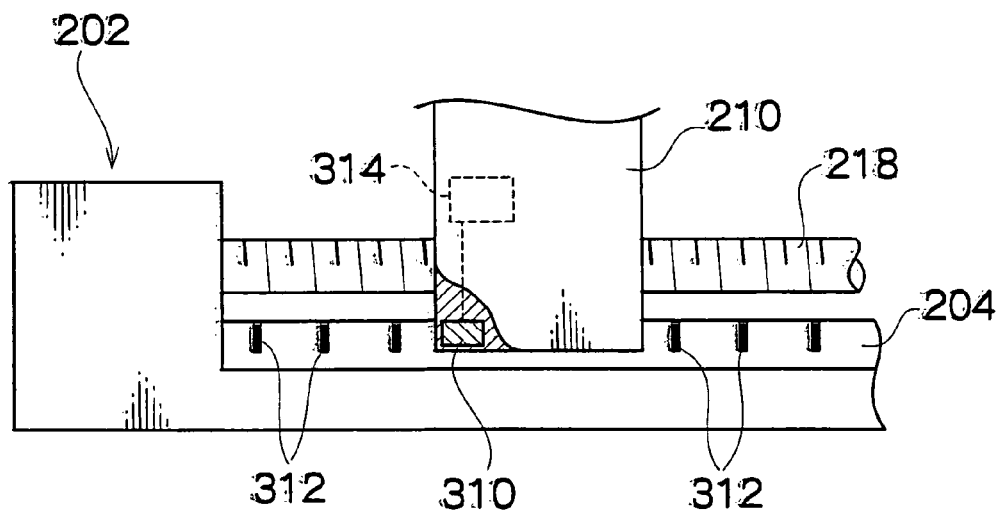
FIG. 12 is a side view of an insertion length measurement device having a different configuration from the configuration in FIG. 6.

FIG. 12 shows another configuration example of an insertion length measurement device. An endoscope holder 210 in FIG. 12 has an optical sensor 310. The optical sensor 310 includes a light emitting element and a light receiving element that are unshown, emits light from the light emitting element toward a guide rail 204, receives the reflected light by the light receiving element, and detects changes of the amount of received light. Tested lines 312 and 312 . . . having a different reflectance from the surroundings are formed on the guide rail 204 at regular intervals. Thus, when the endoscope holder 210 is slid along the guide rail 204, the optical sensor 310 detects the tested lines 312 to allow the amount of movement to be measured by the number of tested lines 312 detected. Therefore, the total insertion length of the insertion portion 12 can be calculated by a calculation device 314.

In the example in FIG. 12, the optical sensor 310 is used, but a magnetic sensor may be provided instead of the optical sensor 310, and magnetic materials may be provided instead of the tested lines 312. In this case, the insertion length of the insertion portion 12 can be measured by detecting the magnetic materials by the magnetic sensor.

Figure 13:
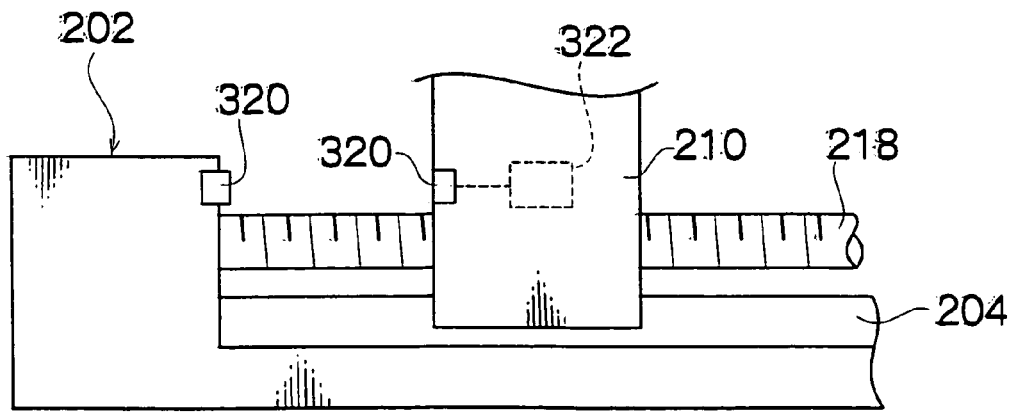
FIG. 13 is a side view of an insertion length measurement device having a different configuration from the configuration in FIG. 6.

Instead of measuring the insertion length of the insertion portion 12, the number of insertion of the insertion portion 12 may be measured to calculate the insertion length of the insertion portion 12 based on the measurement value. For example, an endoscope holder 210 and a stage 202 in FIG. 13 have a pair of contact sensors 320 and 320 that detect contacts, and a calculation device 322 is connected to one of the contact sensors 320 and 320. The calculation device 322 counts the number of contacts of the pair of contact sensors 320 and 320, and the counted number is multiplied by a stroke in one insertion to obtain the total insertion length. The total insertion length may be calculated in this way.

In the embodiment, the insertion length of the insertion portion 12 is calculated by measuring the amount of movement of the endoscope holder 210, but not limited to this, the amount of movement of the auxiliary member holder 230 may be measured to calculate the insertion length of the insertion auxiliary member 70. The insertion length of the insertion auxiliary member 70 is substantially equal to the insertion length of the insertion portion 12, thereby allowing calculation of the total insertion length.

In the embodiment, the endoscope holder 210 and the auxiliary member holder 230 are slid using the feed screw mechanism, but the driving device for the endoscope holder 210 and the auxiliary member holder 230 is not limited to this, and other driving devices such as an air cylinder or a rack and pinion mechanism may be used to slide the endoscope holder 210 and the auxiliary member holder 230.

In the embodiment, the insertion and removal of the insertion portion 12 and the insertion auxiliary member 70, and the expansion and contraction of the first balloon 42 and the second balloon 72 are all automated, but not limited to this, these operations may be manually performed in part. For example, the insertion of the insertion portion 12 (that is, sliding of the endoscope holder 210 in an advance direction) only may be manually performed. In this case, the operator manually inserts the insertion portion 12 of the endoscope 10, and thus can insert the insertion portion 12 while observing the inside of the intestine 90.

The insertion and removal of both the insertion portion 12 and the insertion auxiliary member 70 may be manually operated by the operator. Specifically, the endoscope holder 210 and the auxiliary member holder 230 are slidably supported by the guide rail 204 of the stage 202, and the operator slides the endoscope holder 210 or the auxiliary member holder 230 as required. This also eliminates the need for the operator to hold the endoscope 10 or the insertion auxiliary member 70, thereby reducing burdens on the operator and allowing the operator to operate the endoscopic device by himself/herself. The insertion portion 12 or the insertion auxiliary member 70 can be linearly guided and inserted into the patient 1, thereby allowing smooth insertion of the insertion portion 12 or the insertion auxiliary member 70 to reduce burdens on the patient 1.

When manually moved by the operator, the endoscope holder 210 or the auxiliary member holder 230 preferably has a handle. For example, a ring-shaped handle 330 is mounted to an endoscope holder 210 in FIG. 14A. The handle 330 is formed to be larger than the ring portion 212 so that the operator can grip the handle 330 at any direction. A bar-shaped handle 332 is provided on a side of an endoscope holder 210 in FIG. 14B. Sliding of the endoscope holder 210 can be also easily performed with such a handle 332.

The holding device 200 in the embodiment linearly guides the endoscope 10 and the insertion auxiliary member 70, but not limited to the linear guiding, a holding device may movably hold an endoscope 10 and an insertion auxiliary member 70.

Figure 15:
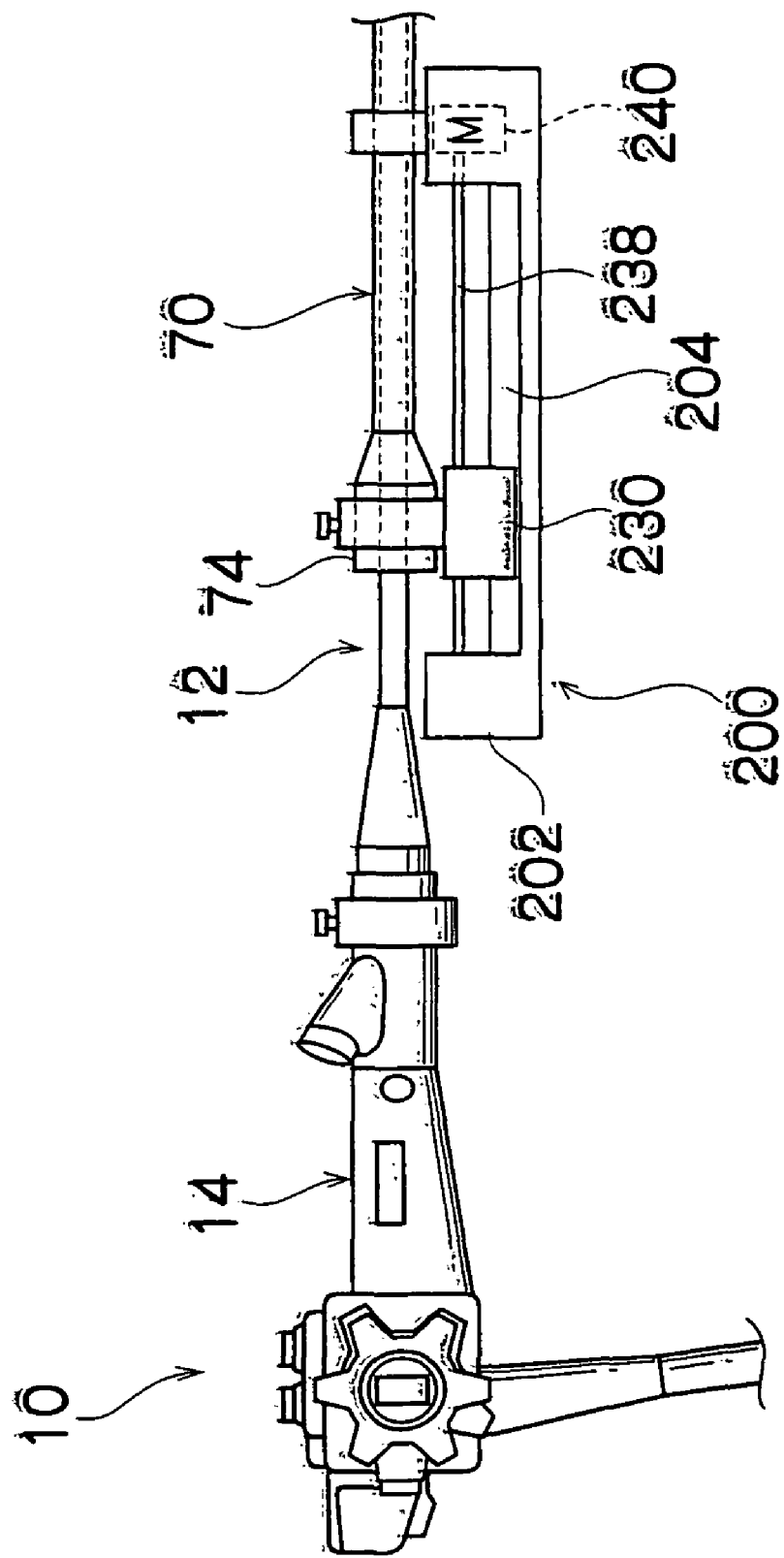
FIG. 15 is a side view of a holding device for an insertion auxiliary member.

In the embodiment, both the endoscope 10 and the insertion auxiliary member 70 are held by the holding device 200, but one of the endoscope 10 and the insertion auxiliary member 70 only may be held. For example, in a holding device in FIG. 15, an auxiliary member holder 230 only is slidably supported by a guide rail 204 of a stage 202 to hold an insertion auxiliary member 70 only. With such a holding device, the operator may grip a hand operation portion 14 of an endoscope 10 only and does not need to grip the insertion auxiliary member 70. This allows the operator to operate the endoscopic device by himself/herself. The insertion auxiliary member 70 held by the holding device in FIG. 15 may be linearly inserted to allow smooth insertion of the insertion auxiliary member 70 and relieve pain in the patient 1. Further, an insertion portion 12 is inserted into the insertion auxiliary member 70 linearly guided to allow smooth insertion of the insertion portion 12.

Figure 16:
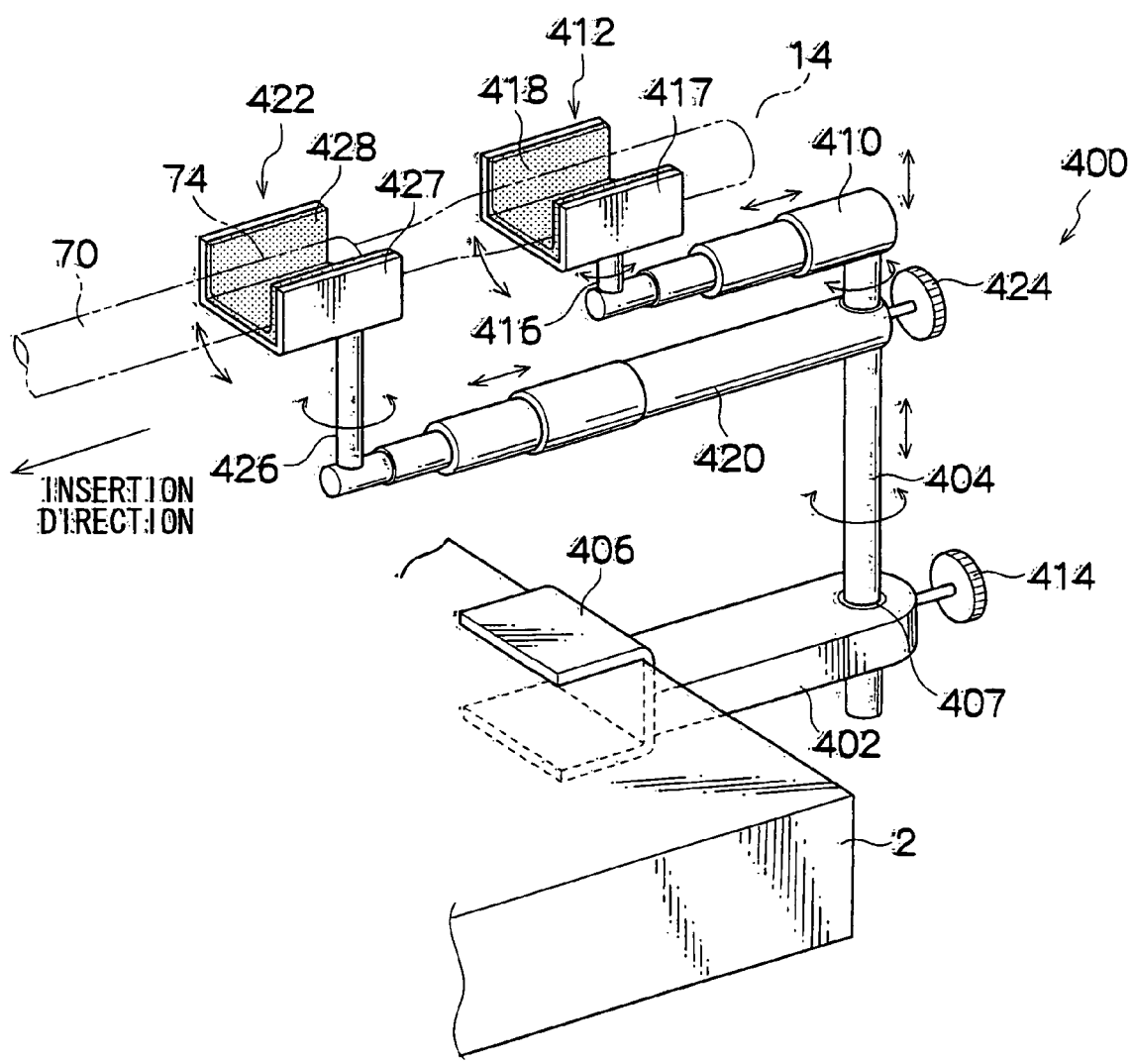
FIG. 16 is a perspective view of a second embodiment of a holding device.

Next, a second embodiment of a holding device according to the invention will be described. As shown in FIG. 16, a holding device 400 according to the second embodiment includes a securing base 402, a column 404, arms 410 and 420 provided perpendicularly to the column 404, and holders 412 and 422 provided at tips of the arms 410 and 420. The securing base 402 has a clamp 406 and is secured to an examination table 2 by the clamp 406 holding the examination table 2. The securing device of the securing base 402 is not limited to the clamp 406, and other securing methods such as a magnetic force or a screw may be used.

The column 404 is vertically provided and passed through a through hole 407 formed in the securing base 402, and secured to the securing base 402 by fastening a securing screw 414. The column 404 may be vertically moved by loosing the securing screw 414.

The lateral arm 410 is secured to an upper end of the column 404. The height of the arm 410 may be adjusted by vertically moving the column 404 with respect to the securing base 402.

The lateral arm 420 is vertically movably mounted to the column 404, and secured at any height by fastening an adjustment screw 424.

The arms 410 and 420 each have a plurality of cylindrical members nested so as to laterally telescope. Bar-shaped connectors 416 and 426 are vertically mounted to the tips of the arms 410 and 420. The connectors 416 and 426 are supported rotatably around vertical axes, and the holders 412 and 422 are tiltably mounted on the connectors 426 and 426. Moderate frictional forces act in the telescoping of the arms 410 and 420, the rotation of the connectors 416 and 426, and the tilt of the holders 412 and 422, and these members can be secured at any positions.

Figure 17:
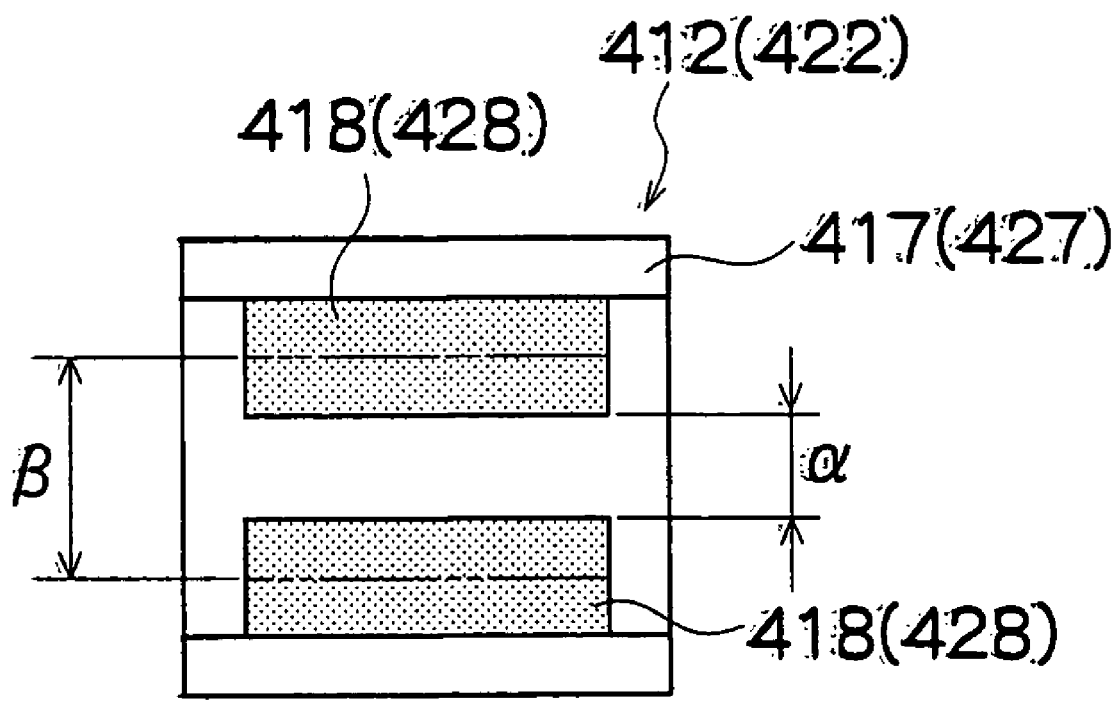
FIG. 17 is a plan view of a holder in FIG. 16.
Figure 18:
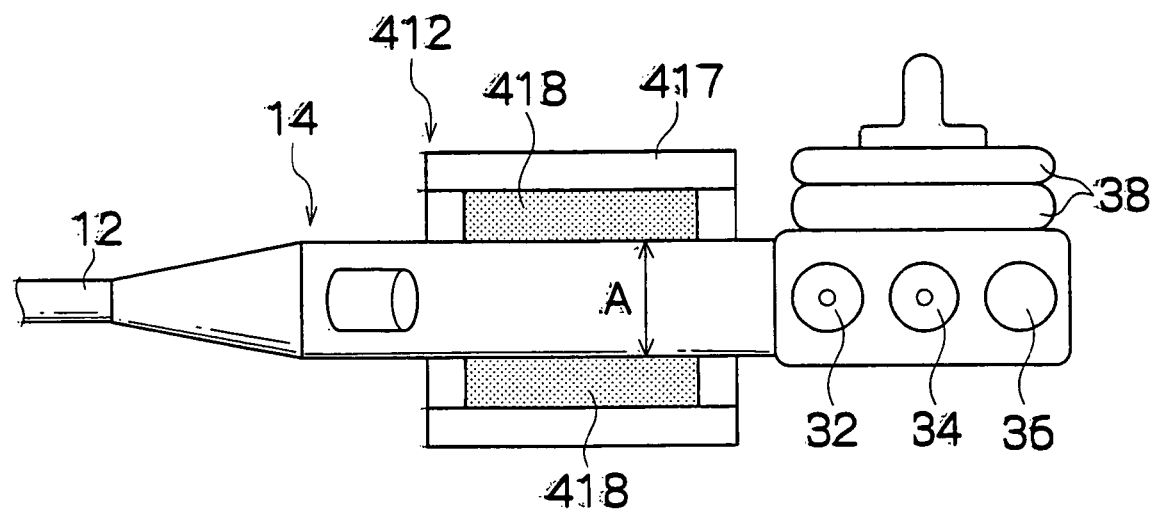
FIG. 18 is a plan view of a holder that holds a hand operation portion of an endoscope.

The holders 412 and 422 include metal supports 417 and 427 formed into a substantial Π shape, and elastic bodies 418 and 428 such as rubber or sponge mounted to the insides of the supports 417 and 427. The elastic bodies 418 and 428 are set to satisfy the following condition so that a hand operation portion 14 of an endoscope 10 or a base end 74 of an insertion auxiliary member 70 can be held by elastic forces thereof. Specifically, the elastic bodies 418 and 428 are set to satisfy expressions $\alpha<A<\beta$ and $\alpha<B<\beta$, where $\alpha$ is a space between the elastic bodies 418 and 428 in a natural state (see FIG. 17), $\beta$ is a space at the time of maximum deformation, A is a width of the hand operation portion 14 (see FIG. 18), and B is a width of the base end 74 of the insertion auxiliary member 70. Such elastic bodies 418 and 428 are mounted to allow the hand operation portion 14 or the base end 74 to be simply fitted into the holders 412 and 422 from above and held. Also, the hand operation portion 14 or the base end 74 can be simply withdrawn upward and removed from the holders 412 and 422. Further, the holders 412 and 422 are formed into a substantially Π shape, and when the hand operation portion 14 and the base end 74 are moved while being held by the holders 412 and 422, the movement direction is restricted to one direction (for example, an insertion direction) by the holders 412 and 422. The configurations of the holders 412 and 422 are not limited to this as long as the endoscope 10 or the insertion auxiliary member 70 may be held.

In the holding device 400 thus configured, an insertion portion 12 of the endoscope 10 and the insertion auxiliary member 70 are inserted into a patient 1, and then the hand operation portion 14 of the endoscope 10 and the base end 74 of the insertion auxiliary member 70 are fitted into the holders 412 and 422 and held. Then, the arm 410 or the arm 420 are telescoped to move the insertion portion 12 or the insertion auxiliary member 70 and push the insertion portion 12 and the insertion auxiliary member 70 into a body cavity of the patient 1. Thus, according to the embodiment, there is no need for an operator to grip both the endoscope 10 and the insertion auxiliary member 70 for operation, thereby allowing an operation by the operator by himself/herself.

According to the embodiment, the holders 412 and 422 are tilted with respect to the connectors 416 and 426, or the connectors 416 and 426 are rotated, thereby allowing angles in the insertion direction of the hand operation portion 14 and the base end 74 held by the holders 412 and 422 to be freely changed. The heights of the arms 410 and 420 are adjusted, or the arms 410 and 420 are telescoped, thereby allowing the positions of the holders 412 and 422 to be freely adjusted and allowing an insertion position into a patient 1 to be freely adjusted. Thus, according to the embodiment, the insertion direction and the insertion position of the endoscope 10 and the insertion auxiliary member 70 can be freely adjusted, and thus the endoscope 10 and the insertion auxiliary member 70 can be set so as to be easily inserted into the patient 1, thereby significantly reducing burdens on the patient 1.

In the above described embodiment, the telescoping and the adjustment of the heights of the arms 410 and 420, the rotation of the connectors 416 and 426, and the tilt of the holders 412 and 422 are manually performed, but these operations may be automatically performed by a driving device such as a motor or a cylinder. In this case, the amount of each operation by the driving device may be controlled to adjust the positions or attitudes of the holders 412 and 422.

In the above described embodiment, the endoscope 10 and the insertion auxiliary member 70 are moved while being held by the holders 412 and 422, but the operating method is not limited to this, and the endoscope 10 and the insertion auxiliary member 70 may be fitted into the holders 412 and 422 and held as required, and removed from the holders 412 and 422 when being moved.

Figure 20:
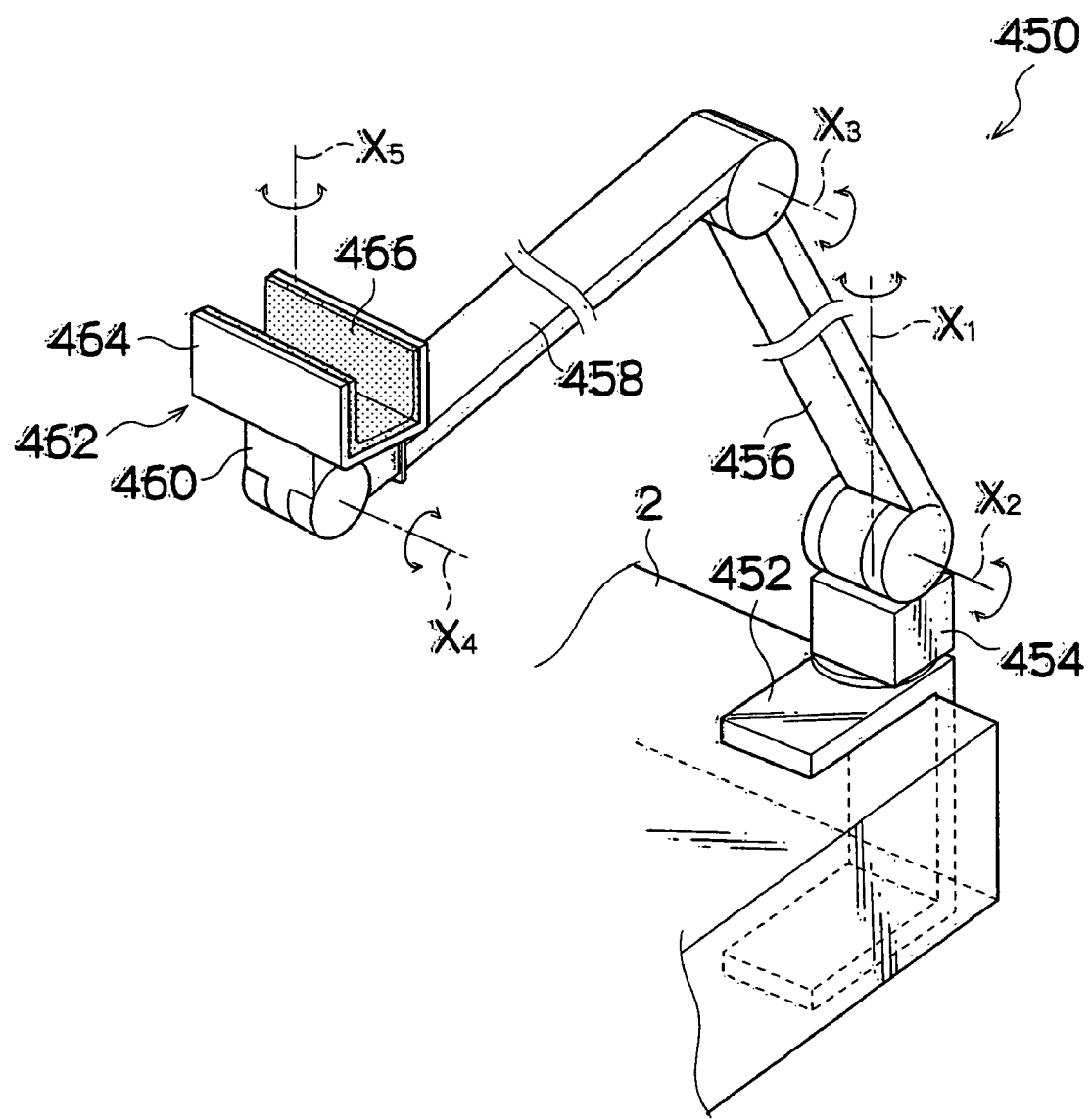
FIG. 20 is a perspective view of a holding device having a different configuration from a configuration in FIG. 16.

FIG. 20 shows an example of a holding device that supports a holder by an arm mechanism different from the arm mechanism in FIG. 16. A holding device 450 in FIG. 20 includes a securing portion 452, a rotation stage 454, arms 456 and 458, a connector 460, and a holder 462. The securing portion 452 is secured to an examination table 2 by holding the examination table 2, and the rotation stage 454 is supported on the securing portion 452 rotatably around a vertical axis $X_1$. A lower end of the arm 456 is supported on the rotation stage 454 rotatably around a lateral axis $X_2$, and the arm 458 is supported on an upper end of the arm 456 rotatably around a lateral axis $X_3$. The connector 460 is supported on a tip of the arm 458 rotatably around a lateral axis $X_4$, and the holder 462 is supported on the connector 460 rotatably around a lateral axis $X_5$.

Figure 19:
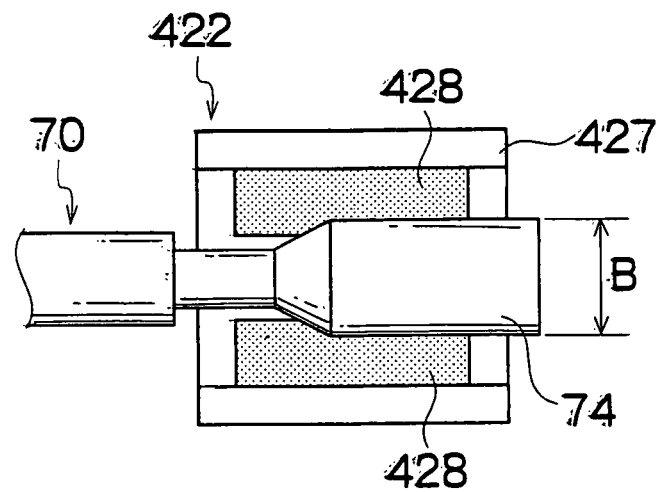
FIG. 19 is a plan view of a holder that holds a base end portion of an insertion auxiliary member.

The holder 462 is formed similarly to the holders 412 and 422 in FIG. 16, and includes a metal support 464 formed into a substantially Π shape, and an elastic body 466 inside the support 464. The elastic body 466 is configured to satisfy expressions $\alpha<A<\beta$ and $\alpha<B<\beta$ like the elastic bodies 418 and 428 in FIGS. 17 to 19 so as to grip both a hand operation portion 14 and a base end 72.

In the holding device 450 thus configured, the arm mechanism that supports the holder 462 has the plurality of rotation axes $X_1$ to $X_5$ to allow the position and the angle of the holder 462 to be freely adjusted. Thus, the holder 462 can be aligned with an insertion port into the patient 1 (the mouth or anus) and positioned in an insertion direction suitable for the patient 1. Therefore, the endoscope 10 and the insertion auxiliary member 70 are held by the holder 462 to allow smooth insertion.

For the holding device 450, one of the endoscope 10 and the insertion auxiliary member 70 is fitted into the holder 462 and held. For example, when the endoscope 10 is moved, the insertion auxiliary member 70 is held by the holder 462, and when the insertion auxiliary member 70 is moved, the endoscope 10 is held by the holder 462. The common holder 462 may be thus used by the endoscope 10 and the insertion auxiliary member 70.

Figure 21:
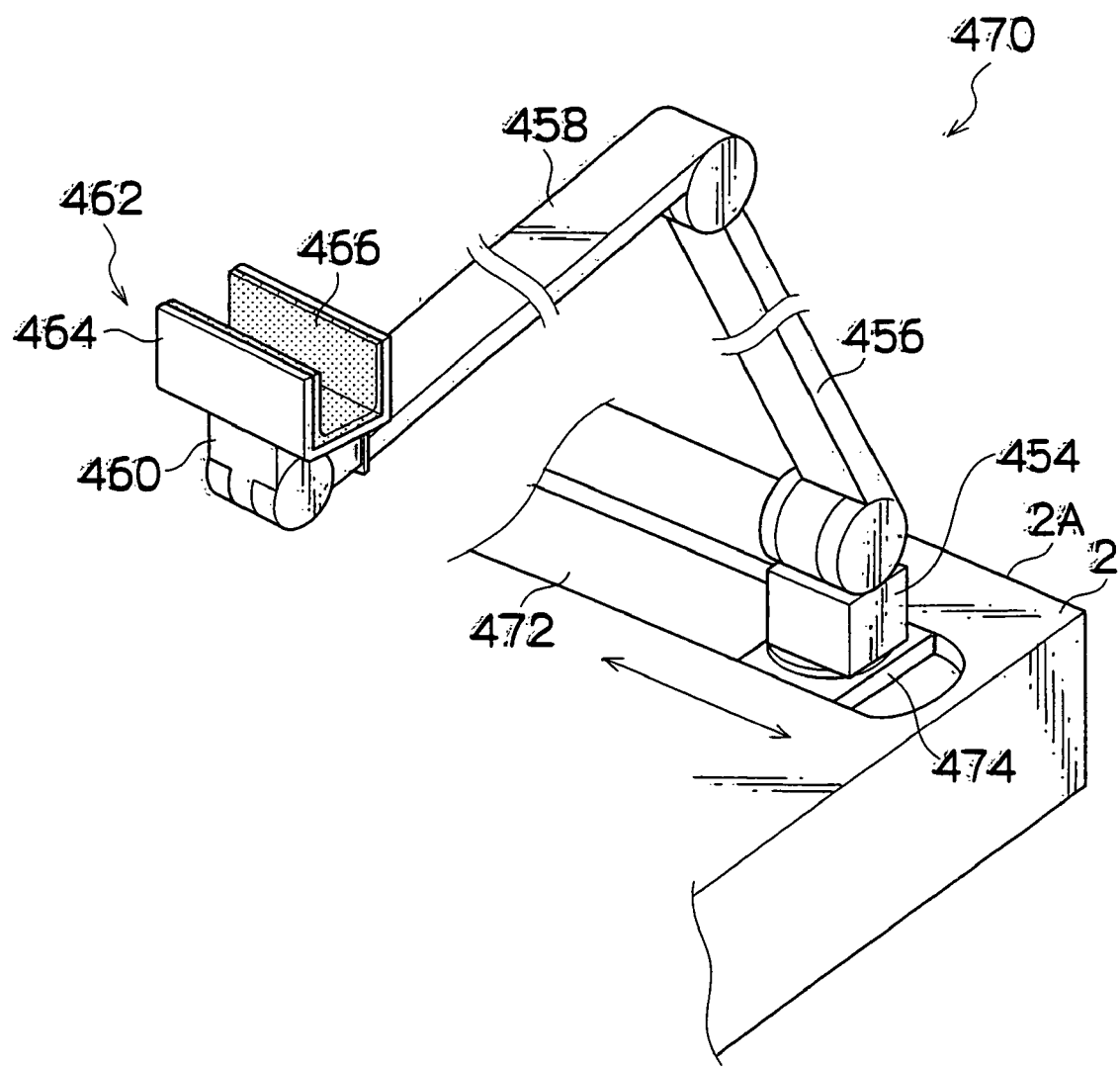
FIG. 21 is a perspective view of a variant of the holding device in FIG. 20.

In the above described embodiment, the holding device 450 is secured to the examination table 2, but not limited to this, the holding device 450 may be adapted to be movable. For example, a holding device 470 in FIG. 21 is adapted to be movable along a guide rail 472 formed on the examination table 2. The guide rail 472 is linearly formed along an edge 2A of the examination table 2, a moving stage 474 is movably mounted along the guide rail 472, and a rotation stage 454 of the holding device 470 is secured to the moving stage 474. An upper configuration of the rotation stage 454 (arms 456 and 458, a connector 460, and a holder 462) is the same as in the holding device 450 in FIG. 20, and a description thereof will be omitted.

In the holding device 470 thus configured, the entire holding device 470 can be moved along the guide rail 472 to allow the holder 462 to be moved within a wider range. The holding device 470 is moved along the guide rail 472 while the endoscope 10 and the insertion auxiliary member 70 are held by the holder 462, thereby allowing the endoscope 10 and the insertion auxiliary member 70 to be moved in the direction of the guide rail 472. This allows push and pull of the endoscope 10 and the insertion auxiliary member 70.

The holding device 470 may be moved manually or automatically. The shape of the guide rail 472 is not limited to the linear shape as long as the shape is suitable for insertion of the endoscope 10 or the insertion auxiliary member 70. For example, the guide rail 472 may be formed to be square along all the edges of an examination table 2. This allows the holder 462 to be placed across the examination table 2.

Figure 22:
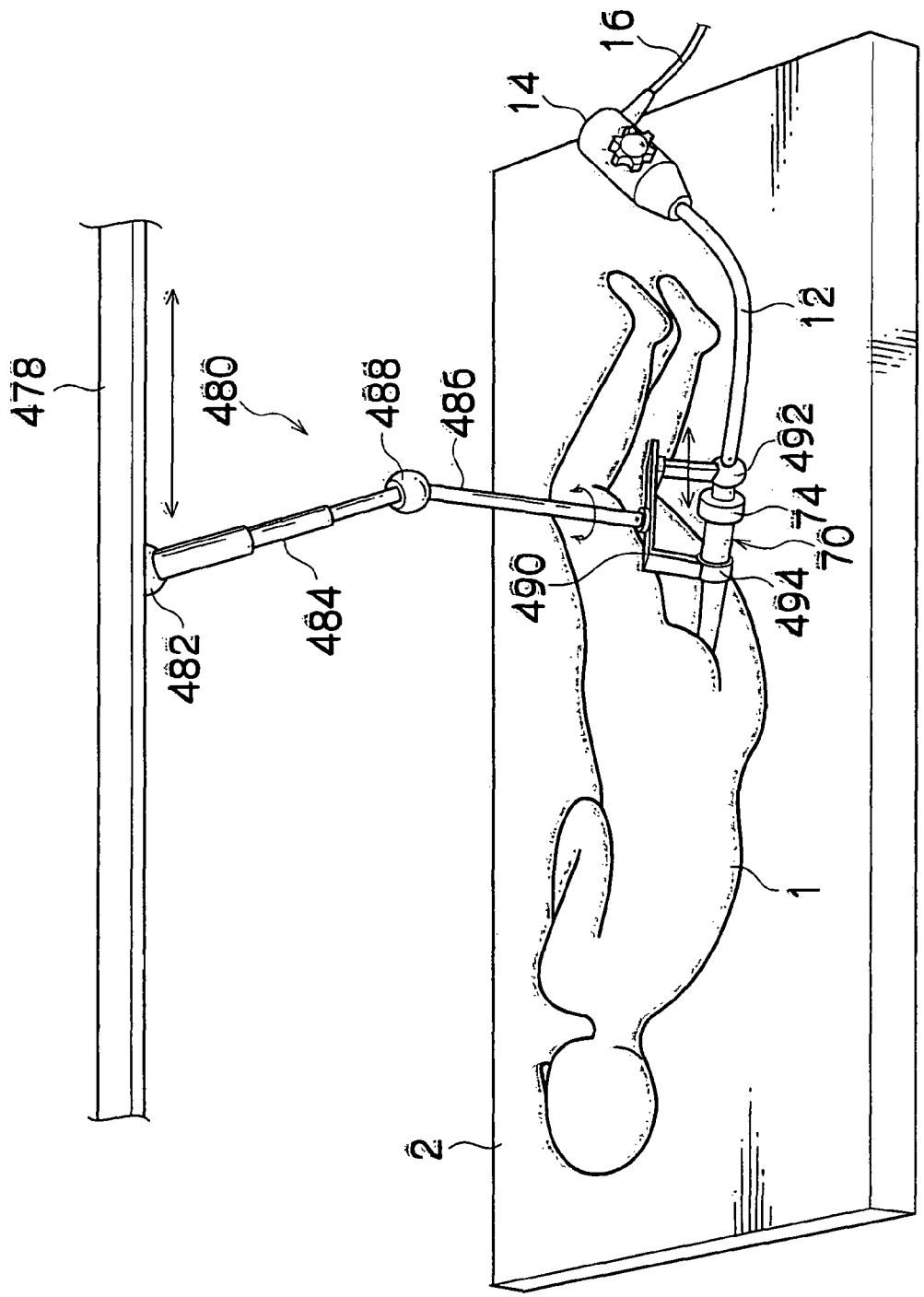
FIG. 22 is a perspective view of a holding device having a different configuration from the configuration in FIG. 16.

In the above described embodiment, the guide rail 472 is formed on the examination table 2, but not limited to this, the guide rail 472 may be formed on the auxiliary table 3 in FIG. 1 or other peripheral devices. Further, as shown in FIG. 22, a guide rail 478 may be placed on a ceiling surface above an examination table 2. In the case shown in FIG. 22, a holding device 480 has a moving portion 482 that moves along the guide rail 478, and an arm 484 is connected to the moving portion 482 via a universal coupling. The arm 484 is nested so as to laterally telescope, and an arm 486 is connected to a tip of the arm 484 via a universal coupling 488. Two holders 492 and 494 are mounted to a lower end of the arm 486 via a space adjustment device 490. The two holders 492 and 494 are supported by the space adjustment device 490 with a space therebetween being adjustable. The holders 492 and 494 are formed into a substantially C shape, and an insertion portion 12 of an endoscope 10 and an insertion auxiliary member 70 can be fitted into the holders 492 and 494, respectively, and held. The space adjustment device 490 is rotatably mounted to the arm 486.

The holding device 480 thus configured can be moved along the guide rail 478 provided on the ceiling surface, thereby allowing the holders 492 and 494 to be moved within a wider range and allowing the holders 492 and 494 to be placed at any position on the examination table 2. In the holding device 480, the holders 492 and 494 can be retracted upward during nonuse. Further, in the holding device 480, the space between the holders 492 and 494 is adjusted by the space adjustment device 490 to allow push and pull of the endoscope 10 or the insertion auxiliary member 70, thereby allowing the endoscope 10 or the insertion auxiliary member 70 to be smoothly inserted into the patient 1.

In the holding device 480, the movement of the moving portion 482, the telescoping of the arm 484, the rotation at both ends of the arms 484 and 486, and the space adjustment of the holders 492 and 494 may be automatically performed using a driving device such as a motor or a cylinder.

Figure 23:
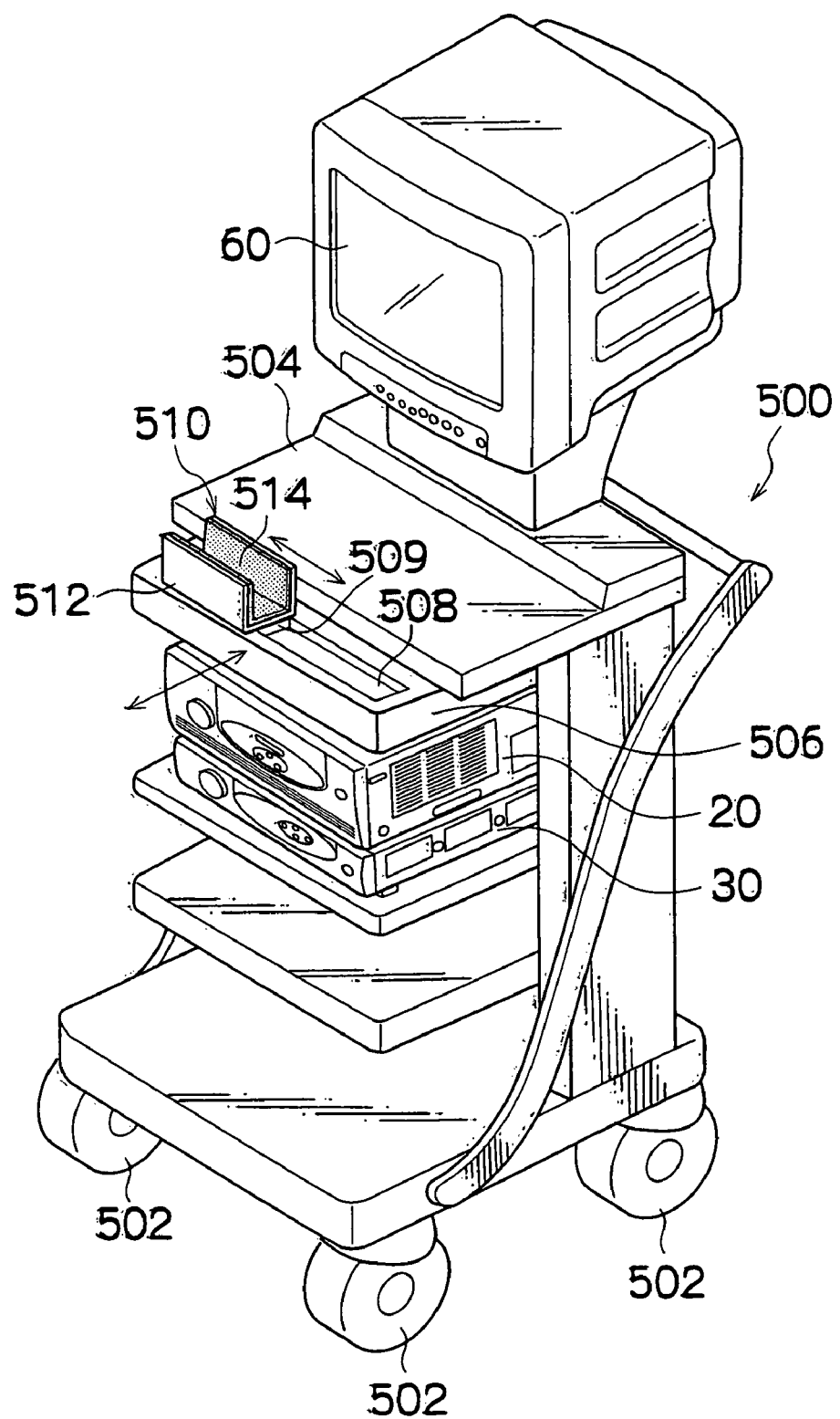
FIG. 23 is a perspective view of a third embodiment of a holding device.

FIG. 23 is a perspective view of a third embodiment of a holding device. The holding device according to the third embodiment in FIG. 23 is formed integrally with a cart 500. The cart 500 is a hand truck on which a light source device 20, a processor 30, and a monitor 60 are placed, has wheels 502 and 502, and is adapted to be movable. Unshown lock mechanisms are mounted to the wheels 502 to secure the cart 500. The cart 500 includes a secured table 504 and a moving table 506 that can be drawn forward, and a guide rail 508 is formed on the moving table 506 laterally (that is, perpendicularly to a movement direction of the moving table 506). A traveling member 509 is mounted to the guide rail 508 so as to be movable along the guide rail 508, and a holder 510 is mounted to the traveling member 509. The traveling member 509 is automatically moved along the guide rail 508 by an unshown driving device. The moving table 506 is automatically moved relative to the secured table 504 by an unshown driving device. The traveling member 509 and the moving table 506 may be manually moved.

Like the holder 462 in FIG. 21, the holder 510 includes a support 512 formed into a substantially Π shape, and an elastic body 514 mounted to the inside of the support 512, and a hand operation portion 14 of an endoscope 10 or a base end 74 of an insertion auxiliary member 70 may be fitted into the holder 510 and held.

For the cart 500 thus configured, the wheels 502 are moved so that the holder 510 is placed near an insertion port (the mouth or anus) into a patient 1 and locked. Then, the endoscope 10 or the insertion auxiliary member 70 inserted into the patient 1 is fitted into the holder 510 and held as required. This eliminates the need for an operator to grip the endoscope 10 or the insertion auxiliary member 70 to allow an operation by the operator by himself/herself. An insertion direction of the endoscope 10 or the insertion auxiliary member 70 may be adjusted by moving the moving table 506. The traveling member 509 is moved along the guide rail 508 to allow the endoscope 10 or the insertion auxiliary member 70 held by the holder 510 to be moved in the insertion direction. This allows the endoscope 10 or the insertion auxiliary member 70 to be automatically inserted into the patient 1.

In the above described embodiment, two holders 510 may be provided so that both the holders 510 move along the guide rail 508. This allows the endoscope 10 and the insertion auxiliary member 70 to be held by the two holders 510, and both the endoscope 10 and the insertion auxiliary member 70 may be automatically moved.

In the above described embodiment, the holder 510 can be moved along the guide rail 508, but not limited to this, the holder 510 may be secured to the moving table 506 or the secured table 508. Also in this case, the cart 500 is moved to allow adjustment of the position of the holder 510. Further, the holder 510 may be removably mounted to the moving table 506 or the like by a fit or magnetic attachment. When the holder 510 is thus adapted to be removable, the holder 510 can be moved to any position while holding the endoscope 10 or the insertion auxiliary member 70. Thus, the holder 510 may be placed in a position suitable for insertion into the patient 1, or once retracted to a position without disturbing an examination. The holders 210 and 230 in FIG. 4, the holders 412 and 422 in FIGS. 16 and 20, or the holder 462 in FIG. 20 may be adapted to be removable, and the holders 210, 230, 412, 422, and 462 may be removed and fitted to the cart 500 or the examination table 2.

Figure 24:
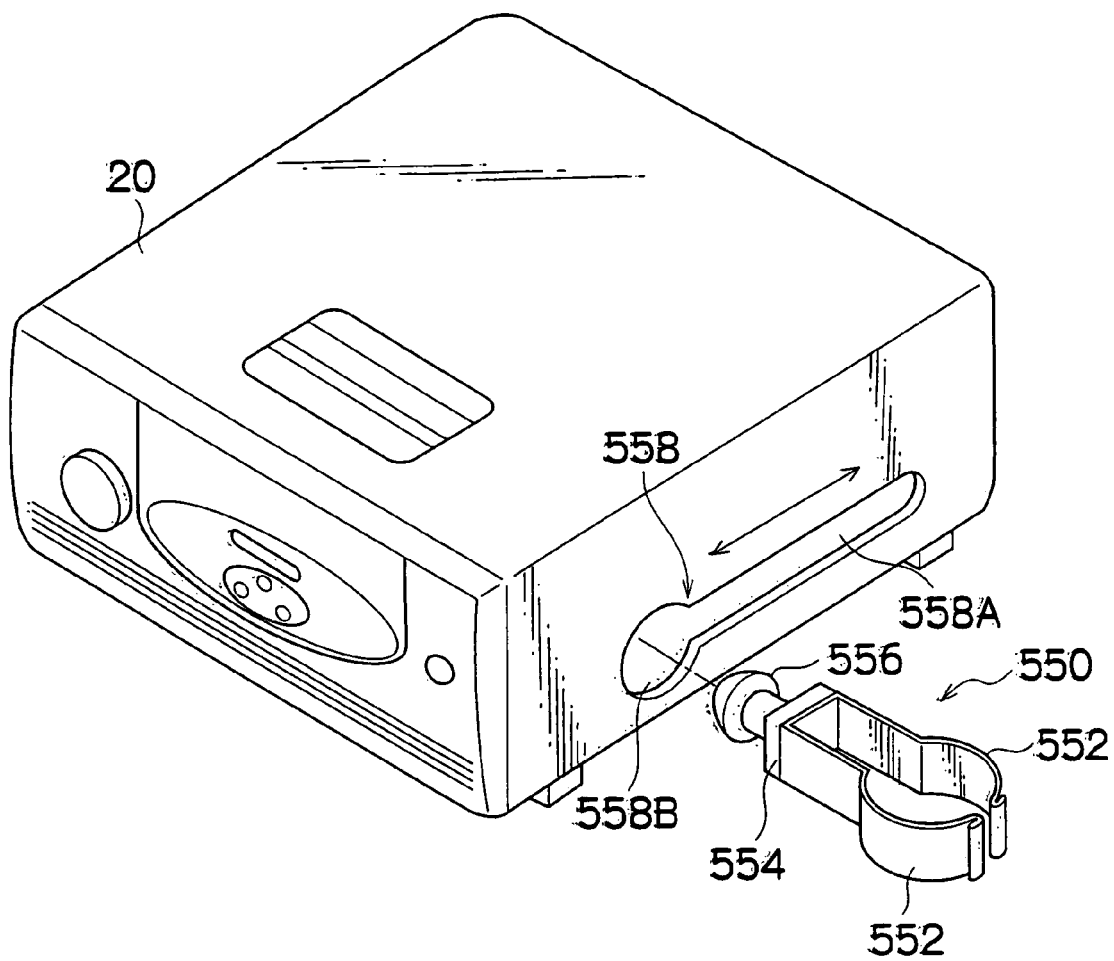
FIG. 24 is a perspective view of a fourth embodiment of a holding device.

FIG. 24 is a perspective view of a fourth embodiment of the holding device. A holder 550 in FIG. 24 has a pair of facing holding plates 552, and the pair of holding plates 552 are mounted to a fixture 554 with a predetermined space. The pair of holding plates 552 may be elastically deformed outward, and an endoscope 10 or an insertion auxiliary member 70 is fitted between the pair of holding plates 552 to hold the endoscope 10 or the insertion auxiliary member 70 between the pair of holding plates 552. The holding plates 552 are curved into an outward arcuate shape, and the endoscope 10 or the insertion auxiliary member 70 is held in the arcuate portion and held.

The holder 550 is removably mounted to and movably supported on a side surface of a light source device 20. Specifically, a substantially hemispherical protruding portion 556 is provided on the fixture 554 of the holder 550, and the protruding portion 556 is inserted into an opening 558 in the side surface of the light source device 20. The opening 558 is constituted by a slit opening 558A elongated in the direction of arrow, and a mounting opening 558B widely opening in an end of the slit opening 558A. The holder 550 is movably supported in the direction of arrow by inserting the protruding portion 556 into the mounting opening 558B and moving the protruding portion 556 along the slit opening 558A. In the light source device 20, a fitting member (not shown) into which the protruding portion 556 is fitted is provided, and a driving device (not shown) that drives the fitting member in the direction of arrow is also provided. Thus, the holder 550 may be automatically moved in the direction of arrow. The holder 550 may be manually moved.

When the endoscope 10 or the insertion auxiliary member 70 is held by the holder 550 thus configured, the endoscope 10 or the insertion auxiliary member 70 held by the holder 550 may be moved. This allows smooth insertion of the endoscope 10 or the insertion auxiliary member 70.

FIG. 24 shows the example of the holder 550 mounted to the side surface of the light source device 20, but not limited to this, the holder 550 may be mounted to a front surface or a top surface of the light source device 20. The holder 550 may be mounted to a peripheral device such as a processor 30 or a balloon control device 100, or may be mounted to an examination table 2 or the like.

FIG. 24 shows the example of the holder 550 mounted slidably in the direction of arrow, but not limited to this, the holder 550 may be secured to the light source device 20 or the like.

Figure 25:
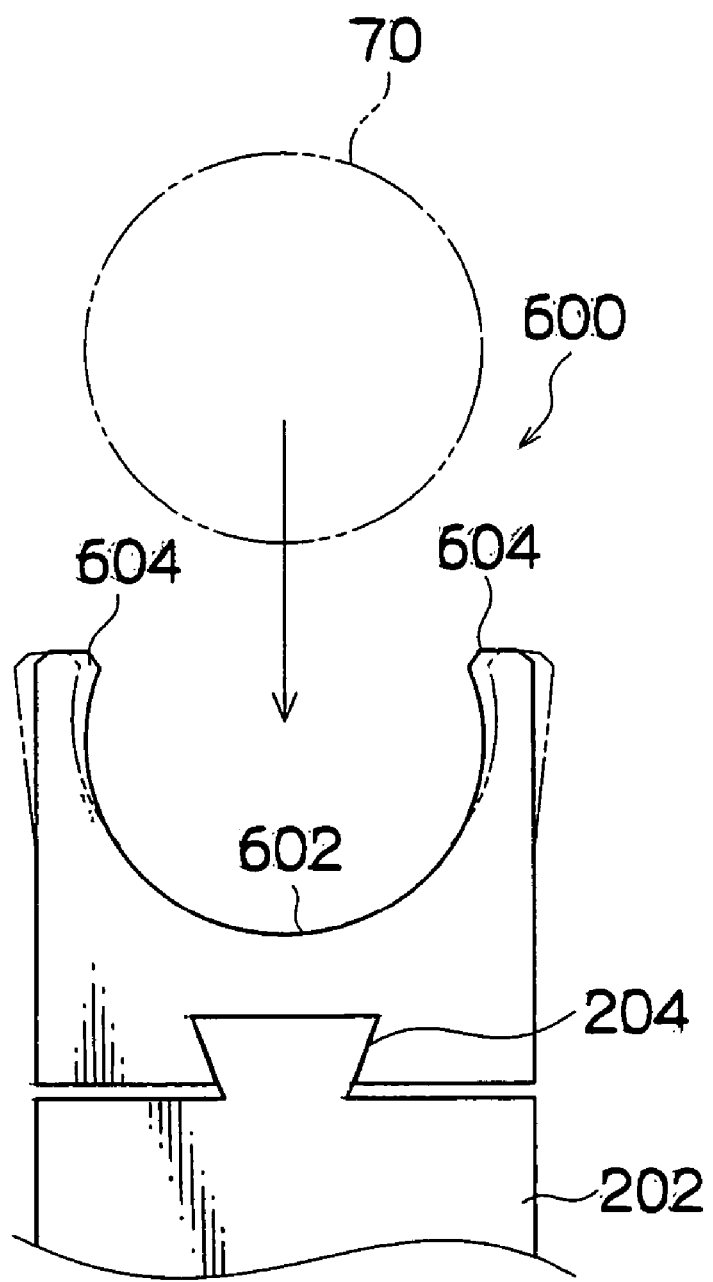
FIG. 25 is a front view of a holder having a different configuration from a configuration in FIG. 5.
Figure 26:
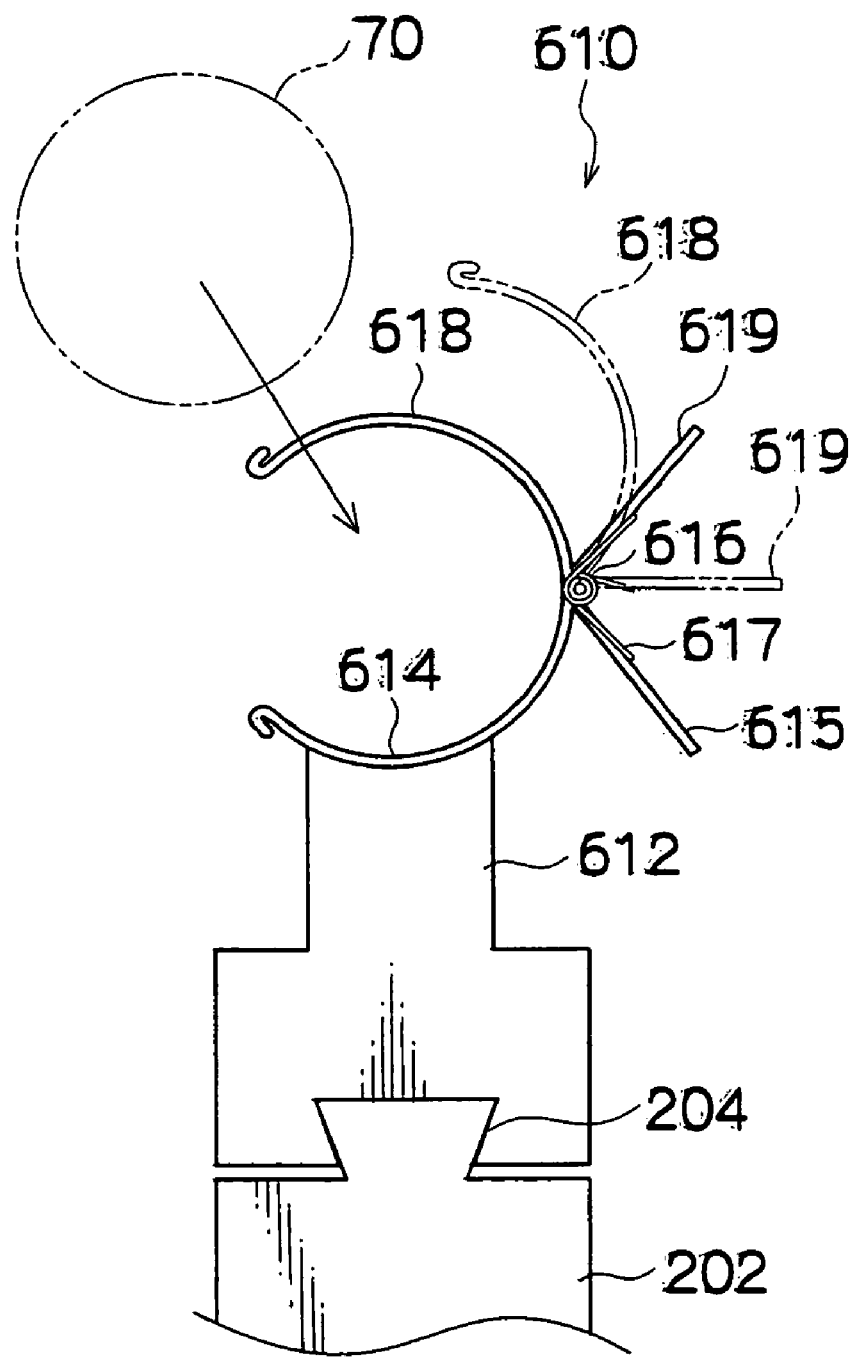
FIG. 26 is a front view of a holder having a different configuration from the configuration in FIG. 5.
Figure 27:
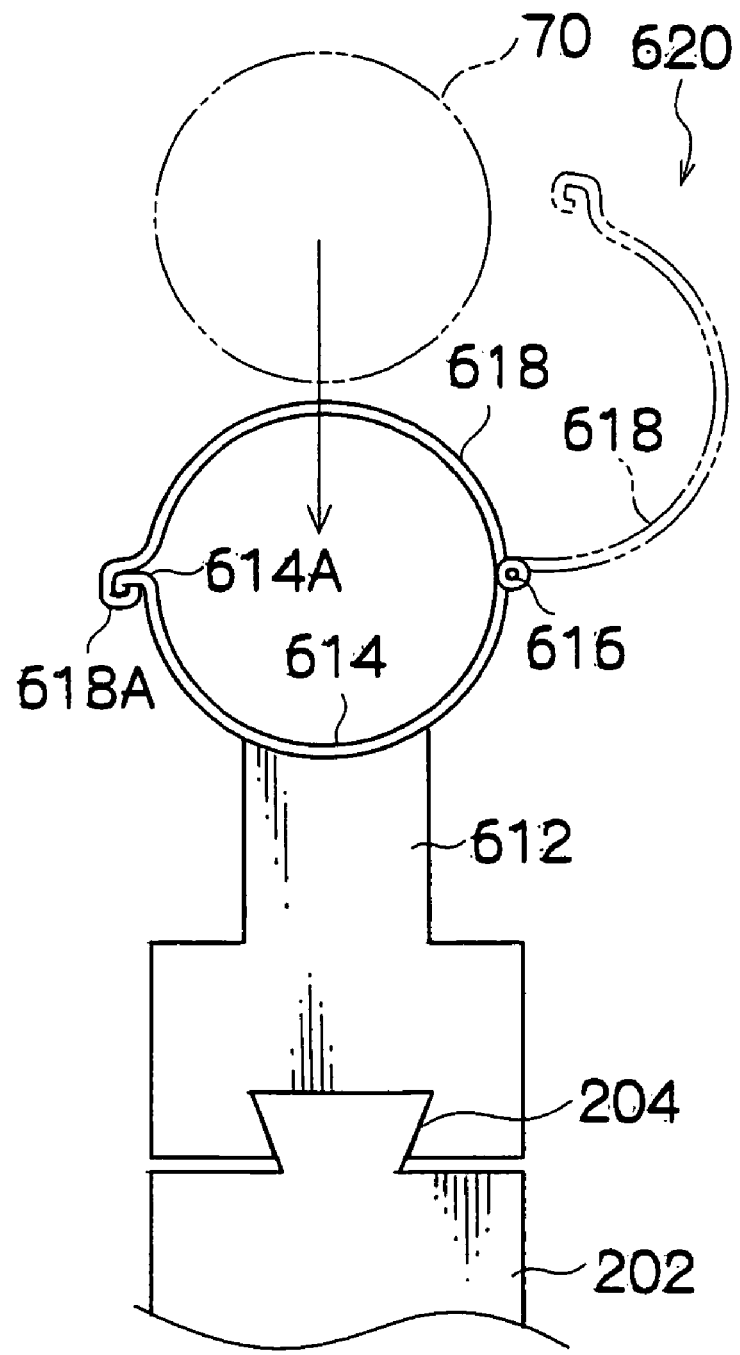
FIG. 27 is a front view of a holder having a different configuration from the configuration in FIG. 5.

FIGS. 25 to 27 show variants of the auxiliary member holder 230 in FIG. 5. A groove 602 having an arcuate section into which an insertion auxiliary member 70 is fitted is formed in an upper surface of a holder 600 in FIG. 25, and a pair of holding portions 604 are formed on both sides of the groove 602. The holder 600 is made of a material that is easily elastically deformed such as plastic, and the holding portions 604 are elastically deformed outward. Thus, when the insertion auxiliary member 70 is fitted into the groove 602 in the holder 600 from above, the pair of holding portions 604 are elastically deformed outward and the insertion auxiliary member 70 is fitted into the groove 602. Then, the pair of holding portions 604 elastically return to the original shape to hold the insertion auxiliary member 70 and held.

A holder 610 in FIG. 26 includes a slide member 612 supported slidably along the guide rail 204, a substantially semicircular secured holding member 614 secured to an upper end of the slide member 612, and a substantially semicircular moving holding member 618 rotatably connected to the secured holding member 614 via a pin 616. Knobs 615 and 619 are formed integrally with the secured holding member 614 and the moving holding member 618, respectively. A spring 617 is mounted between the knobs 615 and 619, and urged in a direction of increasing a space between the knobs 615 and 619 (that is, in a direction of reducing a space between the secured holding member 614 and the moving holding member 618). The holder 610 thus configured first reduces the space between the knobs 615 and 619 against an urging force of the spring 617 to increase the space between the secured holding member 614 and the moving holding member 618. Then, an insertion auxiliary member 70 is placed between the secured holding member 614 and the moving holding member 618. Then, moving an operator's hand off the knobs 615 and 619, the insertion auxiliary member 70 is held by the secured holding member 614 and moving holding member 618 using the urging force of the spring 617. This causes the insertion auxiliary member 70 to be held by the holder 610.

In a holder 620 in FIG. 27, a tip of a secured holding member 614 and a tip of a moving holding member 618 are bent to have fitting portions 614A and 618A that fit each other. Thus, by the holder 620, the fitting portions 614A and 618A can fit each other when an insertion auxiliary member 70 is held by the secured holding member 614 and the moving holding member 618, and the insertion auxiliary member 70 can be firmly held.

Figure 28:
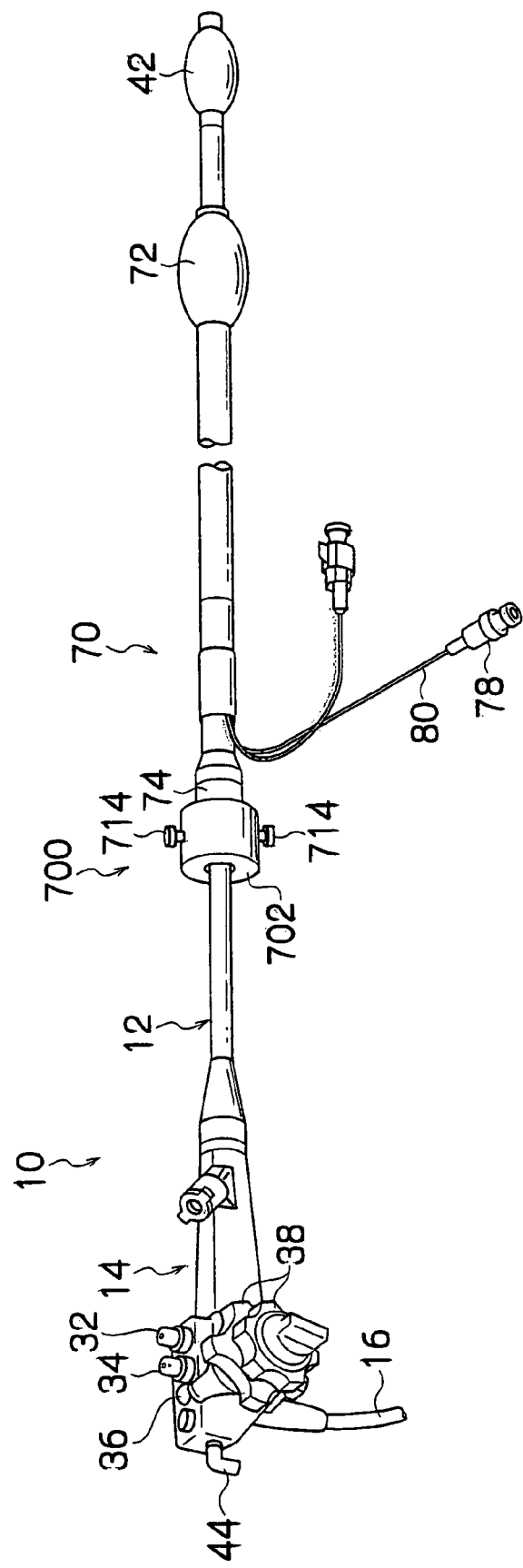
FIG. 28 shows a system configuration of a fourth embodiment of the holding device.
Figure 29:
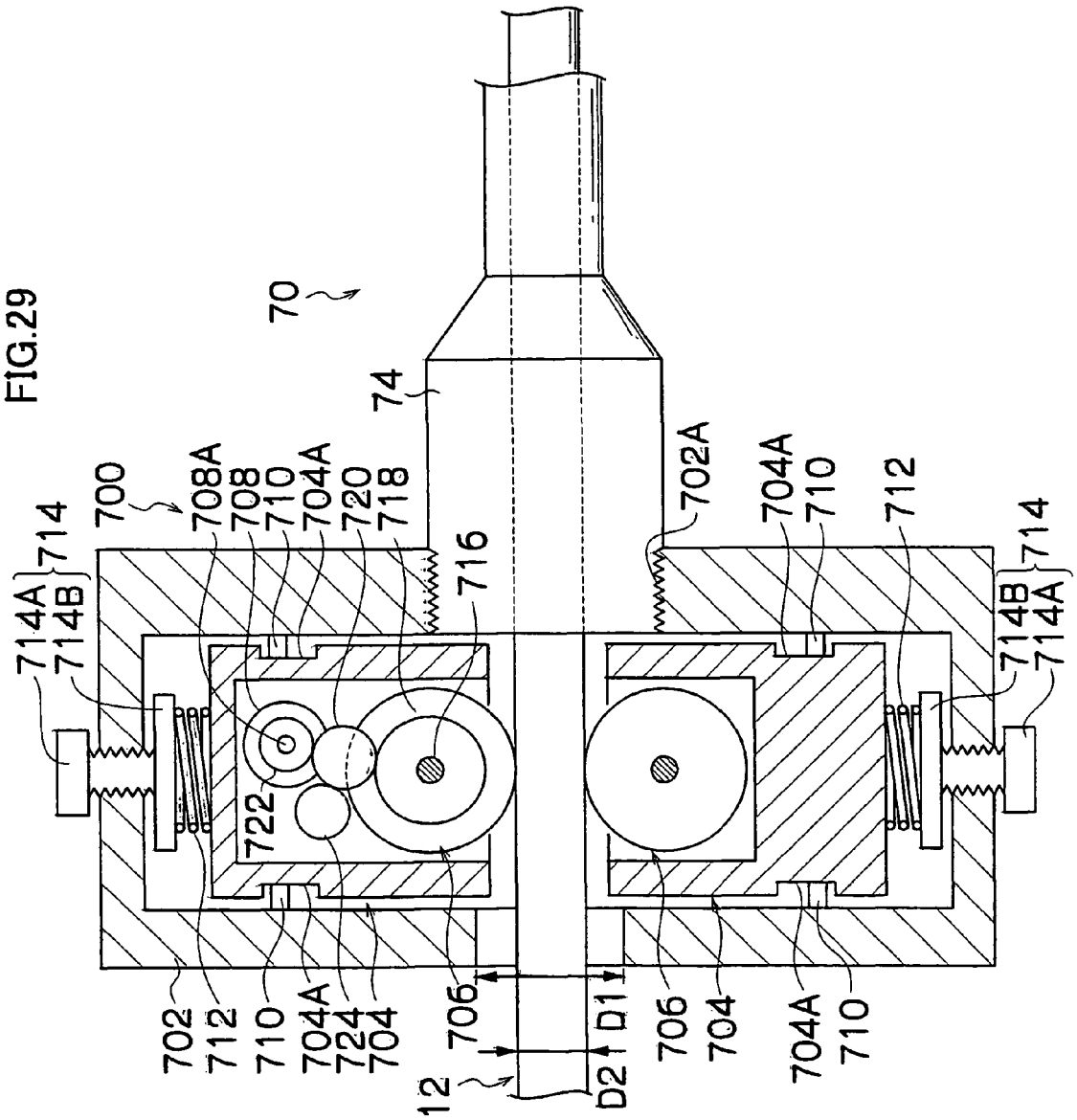
FIG. 29 is a sectional view of a configuration of the holding device in FIG. 28.

FIG. 28 is a perspective view of a configuration of an endoscopic device using a fifth embodiment of a holding device according to the invention. FIG. 29 is a sectional view of the holding device. A holding device 700 shown in FIGS. 28 and 29 is a device that is mounted to an insertion auxiliary member 70 and holds an insertion portion 12 of an endoscope 10.

As shown in FIGS. 28 and 29, the holding device 700 mainly includes a case 702, a slider 704, a roller 706, and a motor 708.

The case 702 is formed into a substantially cylindrical shape, and has an inner diameter D1 larger than an outer diameter D2 of the insertion portion 12 so that the insertion portion 12 can be passed therethrough. The case 702 includes mail threads 702A, which engage a base end 74 of the insertion auxiliary member 70. The case 702 may be removably mounted to the base end 74 of the insertion auxiliary member 70, and may be mounted by a fit or magnetic attachment.

A pair of sliders 704 are provided in the case 702. Grooves 704A are formed in the sliders 704 in a diametrical direction of the case 702, and pins 710 protruding from the case 702 engage the grooves 704A. This allows each slider 704 to be supported slidably in the diametrical direction of the case 702.

A spring 712 is provided outside each slider 704, and each slider 704 is urged inward by the spring 712. An urging force adjustment member 714 is provided outside each spring 712. The urging force adjustment member 714 includes an adjustment screw 714A diametrically threaded into an outer peripheral surface of the case 702, and a pressure plate 714B mounted to a tip of the adjustment screw 714A, and the spring 712 is provided between the pressure plate 714B and the slider 704. By the urging force adjustment member 714, the adjustment screw 714A is rotated to diametrically move the pressure plate 714B to change a space between the pressure plate 714B and the slider 704, thereby adjusting the urging force of the spring 712. This allows adjustment of a pressing force of a below described roller 706 against the insertion portion 12. The urging device is not limited to the spring 712, but an elastic body such as rubber may be used.

The roller 706 is supported by each slider 704. The roller 706 is provided so as to protrude from an inner side surface in a diametrical direction of each slider 704, and is abutted against the insertion portion 12 passed through the case 702. The roller 706 is supported rotatably in an insertion and removal direction of the insertion portion 12. Thus, the roller 706 is abutted against the insertion portion 12 and rotated to allow insertion and removal of the insertion portion 12. An outer peripheral surface of the roller 706 is preferably made of a soft material such as rubber, thereby obtaining sufficient frictional forces with respect to the surface of the insertion portion 12 and preventing damage to the surface of the insertion portion 12.

In one of the sliders 704 (an upper slider 704 in FIG. 29), a gear 718 is mounted to a rotation axis 716 of the roller 706. The gear 718 meshes with a gear 722 via a gear 720, and the gear 722 is mounted to a rotation axis 708A of a motor 708. The motor 708 is secured to the slider 704, and supported slidably in the diametrical direction of the case 702 together with the slider 704. As the motor 708, for example, a stepping motor is used to rotate the rotation axis 708A forward or backward at desired speed. Thus, the motor 708 is driven to rotate the roller 706 forward or backward. Thus, the insertion portion 12 abutted against the roller 706 may be moved in an insertion direction or a withdrawal direction. The forward rotation is a rotation in the insertion direction of the insertion portion 12, and the backward rotation is a rotation in the withdrawal direction of the insertion portion 12. The motor 708 has a safety function of automatically stopping when a load higher than a threshold value is applied, and a lock function of locking the rotation of the rotation axis 708A when the rotation drive is stopped.

Drive control of the motor 708 is performed by a balloon control device 100 (FIG. 7). Specifically, a manual mode is selected by the balloon control device 100, and when an operation button 130a is pressed, the motor 708 is driven to rotate the roller 706 forward, and when an operation button 130b is pressed, the motor 708 is driven to rotate the roller 706 backward. When an automatic mode is selected and operation buttons 132a, 132b, 136a and 136b are pressed, the motor 708 is driven according to operation procedures previously stored to rotate the roller 706 forward or backward. Operation buttons for driving the motor 708 may be provided on the case 702 of the holding device 700. Specifically, an operation button for driving the motor 708, an operation button for stopping the motor 708, and an operation button for switching between forward and backward rotations of the motor 708 may be provided on the outer surface of the case 702 to perform the drive control of the motor 708 by these operation buttons.

An encoder 724 is connected to the gear 720. Thus, the RPM of the gear 720, that is, the RPM of the roller 706 may be measured by the encoder 724. The encoder 724 is connected to an unshown calculation device provided in the slider 704 or the case 702, and the calculation device converts the measurement value of the encoder 724 into the amount of movement of the insertion portion 12 relative to the insertion auxiliary member 70. Then, conversion values are summed to obtain the total insertion length. The total insertion length obtained is displayed, for example, on a total insertion length display portion 120 of a balloon monitor 106 (see FIG. 7). This allows the operator to recognize which position in a body cavity a tip of the insertion portion 12 reach. A display portion may be provided on the outer surface of the case 702, and the insertion length or the total insertion length may be displayed on the display portion.

In the above described embodiment, the driving device is provided in one slider 704 only, but driving devices may be provided in the sliders 704 to rotate the rollers 706 in synchronization with each other.

The numbers of the sliders 704 and the rollers 706 are not limited, but three or more sliders 704 and rollers 706 are preferably provided for stable holding of the insertion portion 12. In this case, the sliders 704 and the rollers 706 are preferably placed at circumferentially regular angular intervals.

In the embodiment, each roller 706 is supported by the slider 704 and diametrically slid, but one of the rollers 706 may be secured.

In the above described embodiment, the rotation of the rotation axis 708A is locked when the motor 708 is stopped, but relative movement between the insertion portion 12 of the endoscope 10 and the insertion auxiliary member 70 may be prevented at the stop of the motor 708. For example, a lock device which locks rotation of the gear 720 or the rotation axis 716 may be provided, or a lock device which locks by abutting a brake member against the insertion portion 12 may be provided.

An operating method of the holding member 700 thus configured will be described.

First, as a preparation, the case 702 of the holding device 700 is fitted to the base end 74 of the insertion auxiliary member 70. Then, the insertion portion 12 of the endoscope 10 is inserted into the insertion auxiliary member 70 from the side of the case 702 of the holding member 700 to place the insertion auxiliary member 70 over the insertion portion 12. Then, the adjustment screw 714A of the urging force adjustment member 714 of the holding member 700 is rotated to adjust an urging force and abut the roller 706 against the insertion portion 12.

After the preparation, operations are performed according to the operation procedures (Step S2 to Step S12) in FIG. 9. Each operation is performed by operating the remote controller 104 or the foot switch 108 in the balloon control device 100 (see FIG. 7).

Among the series of operation procedures, for the insertion (Step S4 and Step S11) of the endoscope 10 (that is, the insertion portion 12), the motor 708 is driven to rotate the roller 706 forward with the insertion auxiliary member 70 being gripped and the operator's hand being moved off the endoscope 10. This causes the insertion portion 12 of the endoscope 10 to be moved relative to the insertion auxiliary member 70 in the insertion direction to automatically insert the insertion portion 12 into the body cavity. The insertion length of the insertion portion 12 is measured by the encoder 724, and the motor 708 is stopped when the measurement value reaches the set value to finish the insertion.

For the push of the insertion auxiliary member 70 (Step S7), the motor 708 is driven to rotate the roller 706 backward with the hand operation portion 14 of the endoscope 10 being gripped and the operator's hand being moved off the insertion auxiliary member 70. This causes the insertion portion 12 to be moved relative to the insertion auxiliary member 70 in the withdrawal direction, but the endoscope 10 is held and thus the holding device 700 travels by itself in the insertion direction along the insertion portion 12 to automatically push the insertion auxiliary member 70 into the body cavity. At this time, the amount of push of the insertion auxiliary member 70 is measured by the encoder 724, and the motor 708 is stopped when the measurement value reaches the set value to finish the push.

For the drawing of the endoscope 10 and the insertion auxiliary member 70 (Step S9), the motor 708 is stopped to prevent rotation of the roller 706. This causes the insertion portion 12 of the endoscope 10 and the insertion auxiliary member 70 to be secured, and thus one of the endoscope 10 and the insertion auxiliary member 70 is simply gripped and drawn to allow both the endoscope 10 and the insertion auxiliary member 70 to be simultaneously drawn. At this time, the stop of the motor 708 causes the lock of the rotation of the roller 706, thereby ensuring that the endoscope 10 and the insertion auxiliary member 70 are secured and simultaneously drawn.

According to the embodiment, the holding member 700 is fitted to the base end 74 of the insertion auxiliary member 70 to hold the insertion portion 12 of the endoscope 10 by the holding member 700, and one of the endoscope 10 and the insertion auxiliary member 70 may be gripped for operation in the insertion of the endoscope 10, the push of the insertion auxiliary member 70, or the drawing of the endoscope 10 and the insertion auxiliary member 70, thereby improving operability.

According to the embodiment, the moving device including the roller 706 and the motor 708 is provided in the holding device 700 to allow the insertion of the endoscope 10 and the push of the insertion auxiliary member 70 to be automatically performed.

According to the embodiment, the slider 704 is provided slidably in the diametrical direction, the roller 706 is supported by the slider 704, and the slider 704 is urged inward by the spring 712, thereby ensuring pressing of the roller 706 against the insertion portion 12. The roller 706 is pressed against the insertion portion 12 of the endoscope 10 for rotation while being urged by the spring 712 to reduce insertion resistance between the insertion portion 12 and the roller 706.

According to the embodiment, the urging force adjustment member 714 is provided to allow adjustment of the urging force for urging the roller 706 against the insertion portion 12, thereby allowing appropriate urging forces to be always applied to the roller 706. The embodiment may be applied to various types of endoscopes 10 having different outer diameters of insertion portions 12.

In the above described embodiment, the case 702 of the holding device 700 may be secured to the examination table 2 or the auxiliary table 3 in FIG. 1, or the cart 500 in FIG. 23. The case 702 may be secured to other devices via the arm mechanism in FIG. 16 or FIG. 21.

The case 702 may be formed integrally with the insertion auxiliary member 70 or incorporated into the insertion auxiliary member 70.

Figure 30:
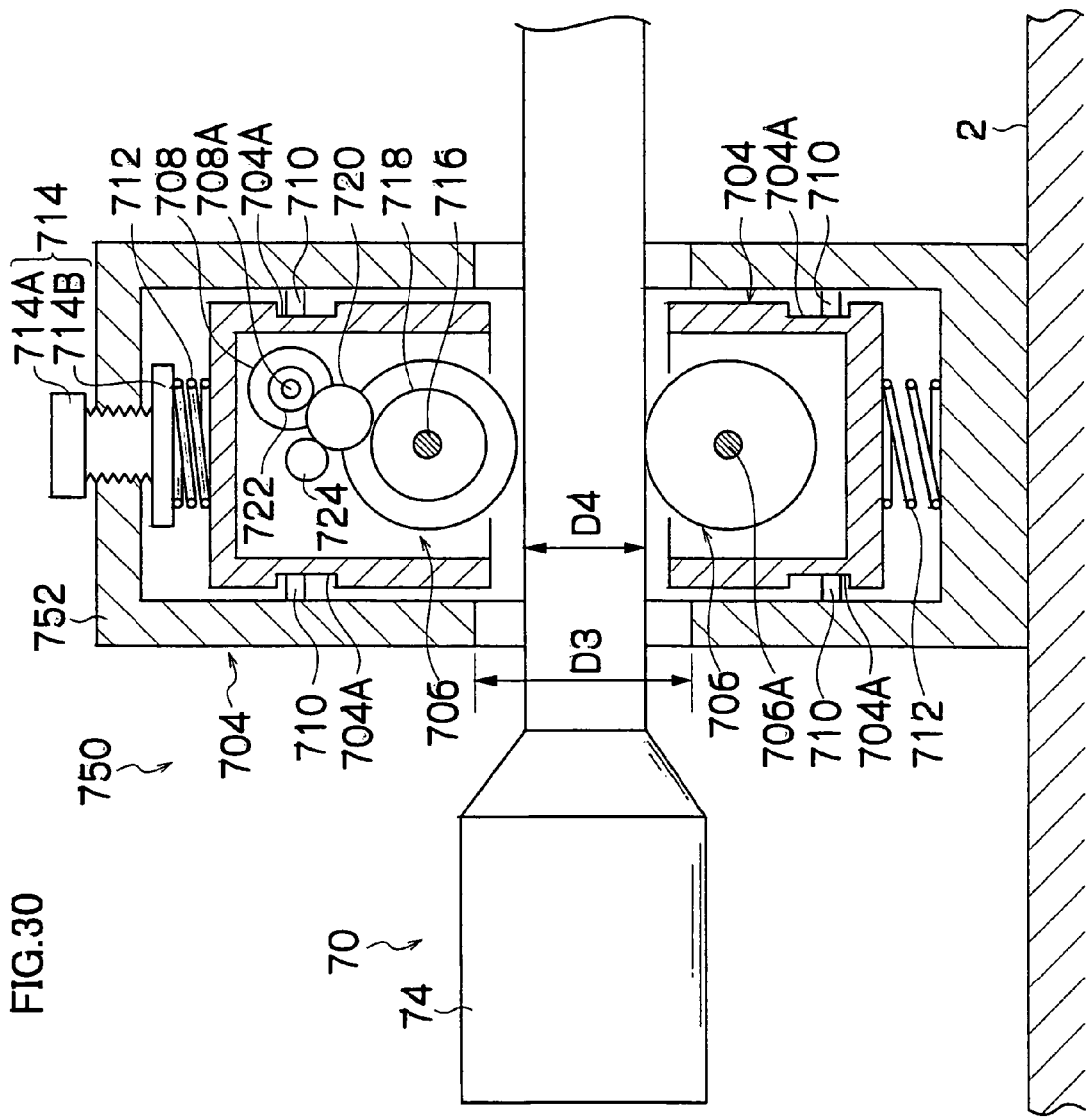
FIG. 30 is a sectional view of a holding device that holds an insertion auxiliary member.

The above described embodiment is the example of the holding device 700 that holds the endoscope 10, but may be applied to a holding device that holds an insertion auxiliary member 70. FIG. 30 is a sectional view of a holding device 750 that holds an insertion auxiliary member 70. A case 752 of the holding device 750 in FIG. 30 is secured to an examination table 2. The case 752 is formed into a substantially cylindrical shape, and has an inner diameter D3 larger than an outer diameter D4 of a tube portion of the insertion auxiliary member 70. Thus, the tube portion of the insertion auxiliary member 70 may be passed through the case 752. For the holding device 750, configurations other than the case 752 are the same as in the holding device 700 in FIG. 29. Specifically, sliders 704 are supported by a case 702 slidably in a diametrical direction, and rollers 706 are rotatably supported by the sliders 704. The sliders 704 are urged inward by springs 712 to abut the rollers 706 against an outer peripheral surface of the insertion auxiliary member 70. A motor 708 is connected to the roller 706, and the motor 708 is driven to rotate the roller 706 forward or backward.

In the holding device 750 thus configured, the motor 708 is driven to rotate the roller 706, thereby allowing the insertion auxiliary member 70 to be inserted into or withdrawn from the body cavity. This allows the push and the drawing of the insertion auxiliary member 70 to be automatically performed.

The holding device 750 in FIG. 30 may be used in combination with the holding device 700 in FIG. 29. This allows the insertion of the endoscope 10, the push of the insertion auxiliary member 70, and the drawing of the endoscope 10 and the insertion auxiliary member 70 to be all automatically performed.

The case 752 of the holding device 750 in FIG. 30 is secured to the examination table 2, but may be secured to other devices. For example, the case 752 of the holding device 750 may be secured to the auxiliary table 3 (see FIG. 1) or the cart 500 (see FIG. 23). The holding device 750 may be secured to other devices via the arm mechanism shown in FIG. 16 or FIG. 21.

Further, the holding device that holds the insertion auxiliary member 70 may be mounted to the endoscope 10. For example, the holding device is provided at a portion of the insertion portion 12 of the endoscope 10 over which the insertion auxiliary member 70 is always placed. As the holding device, it is preferable that a roller protruding from the outer surface of the insertion portion 12 is provided, and the roller is abutted against the inner peripheral surface of the insertion auxiliary member 70 for rotation. This allows the insertion auxiliary member 70 to be held by the endoscope 10, and one of the endoscope 10 and the insertion auxiliary member 70 is gripped to hold both the endoscope 10 and the insertion auxiliary member 70.

Figure 31:
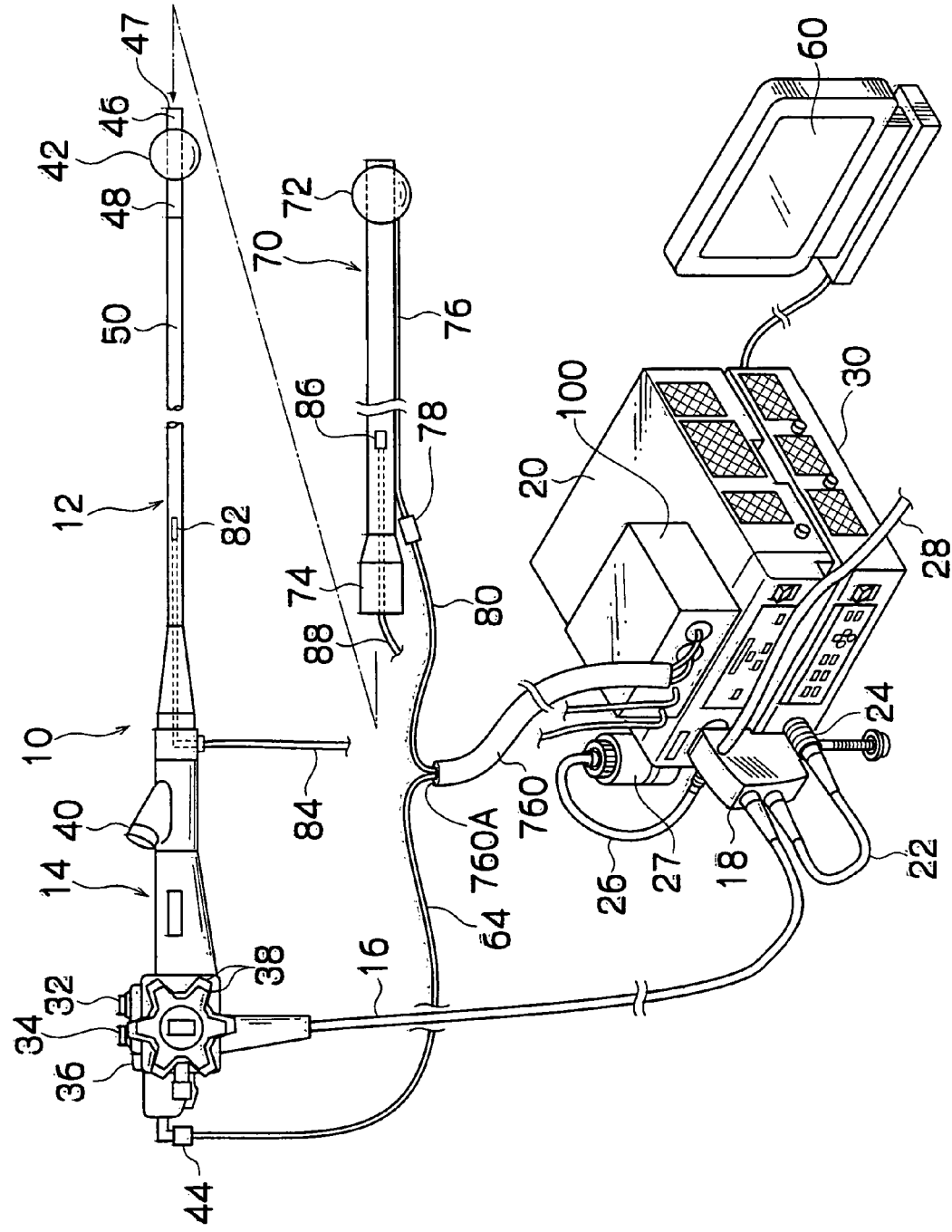
FIG. 31 shows a configuration of an endoscopic device using a protective tube.

FIG. 31 shows a configuration of an endoscopic device that protects tubes 64 and 80 using a protective tube 760. The protective tube 760 in FIG. 31 is a hard tube that ties the tubes 64 and 80 together and surrounds the tubes 64 and 80, for example, a spiral tube made of silicone rubber or a cylindrical tube made of fluororesin. Such a protective tube 760 is used to prevent crushes of the tubes 64 and 80. This prevents occurrence of poor feeding or exhaust of air caused by crushed tubes 64 and 80. Also, the protective tube 760 is used to prevent the tubes 64 and 80 from coming apart and thus prevent the tubes 64 and 80 from being entangled with each other or caught on other devices. At portions exposed from a tip 760A of the protective tube 760, the tube 80 is preferably set to be shorter than the tube 64. The exposed portion of the tube 80 on the side of the insertion auxiliary member 70 is set to be short to eliminate looseness, thereby improving operability. Specifically, looseness of the tube 80 near the base end 74 of the insertion auxiliary member 70 may easily cause entanglement of the tube 80 when the insertion auxiliary member 70 is moved, thereby causing poor operability. However, the exposed portion of the tube 80 is set to be short to prevent looseness of the tube 80, thereby improving operability.

What is claimed is:

1. A balloon control apparatus, comprising:
   an insertion auxiliary member which is bendable and placed over an insertion portion of an endoscope to help insertion of the insertion portion, the insertion auxiliary member having a balloon for the insertion auxiliary member at a tip end thereof that expands and contracts by supplying and sucking air;
   a holding device which has an insertion auxiliary member holder for holding the insertion auxiliary member and an endoscope holder for holding a hand operation portion of the endoscope, a driving device for the insertion auxiliary member to move the insertion auxiliary member in an insertion direction or a withdrawal direction, and a driving device for the endoscope to move the endoscope holder in an insertion direction or a withdrawal direction;
   an air supplying and sucking device for the insertion auxiliary member which supplies and sucks air to and from the balloon for the insertion auxiliary member;
   an operation device; and
   a control device which controls, in accordance with operation of the operation device, driving of the air supplying and sucking device for the insertion auxiliary member and the driving device for the endoscope,
   wherein the operation device includes a step advancement instruction device which instructs advancing of steps so that the predetermined operation steps advance in sequence and;
   wherein the predetermined operation steps comprise:
   a first step of moving, in accordance with a next instruction by the step advancement instruction device to advance steps, the insertion portion in the insertion direction by a predetermined amount by driving the driving device for endoscope to move the endoscope holder in the insertion direction by a predetermined amount;
   a second step of contracting, in accordance with a next instruction by the step advancement instruction device to advance steps, the balloon for insertion auxiliary member by driving the air supplying and sucking device for insertion auxiliary member to suck air from the balloon for insertion auxiliary member;

a third step of moving, in accordance with a next instruction by the step advancement instruction device to advance steps, the insertion auxiliary member in the insertion direction by a predetermined amount by driving the driving device for insertion auxiliary member to move the insertion auxiliary member holder in the insertion direction by a predetermined amount;

a fourth step of expanding, in accordance with a next instruction by the step advancement instruction device to advance steps, the balloon for insertion auxiliary member by driving the air supplying and sucking device for insertion auxiliary member to supply air to the balloon for insertion auxiliary member;

a fifth step of moving, in accordance with a next instruction by the step advancement instruction device to advance steps, the insertion portion and the insertion auxiliary member in a direction opposite to the insertion direction by a predetermined amount by driving the driving device for endoscope and the driving device for insertion auxiliary member to move the endoscope holder and the insertion auxiliary member holder in a direction opposite to the insertion direction by a predetermined amount; and a sixth step of moving, in accordance with a next instruction by the step advancement instruction device to advance steps, the insertion portion in the insertion direction by a predetermined amount by driving the driving device for endoscope to move the endoscope holder in the insertion direction by a predetermined amount;

where after the sixth step, the second to sixth steps are repeated in accordance with a next instruction by the step advancement instruction device to advance steps; and wherein the control device controls, in accordance with the instruction by the step advancement instruction device, driving of the air supplying and sucking device for the insertion auxiliary member, the driving device for the insertion auxiliary member, and the driving device for the endoscope, so that the operation steps advance in sequence.

2. The balloon control apparatus according to claim 1, wherein the operation device includes a mode switching device for switching operation mode to manual operation mode, an air supplying and sucking instruction device for instructing supplying and sucking air to and from the balloon for the insertion auxiliary member, a movement instruction device for insertion auxiliary member holder, and a movement instruction device for the endoscope holder to instruct movement of the endoscope holder, and when operation mode is switched to the manual operation mode, the control device controls, in accordance with instruction by the air supplying and sucking instruction device, the movement instruction device for insertion auxiliary member holder, and the movement instruction device for instructing movement of the endoscope holder, driving of the air supplying and sucking instruction device and the driving device for the insertion auxiliary member, and the movement instruction device for the endoscope holder.

3. The balloon control apparatus according to claim 1, wherein the predetermined operation steps further comprises a step of expanding, in accordance with a next instruction by the step advancement instruction device to advance steps, the balloon for insertion auxiliary member by driving the air supplying and sucking device for insertion auxiliary member to supply air to the balloon for insertion auxiliary member, as a step previous to the first step.

4. A balloon control apparatus, comprising:

an insertion auxiliary member which is bendable and placed over an insertion portion of an endoscope to help insertion of the insertion portion, wherein the endoscope has a first balloon which is placed at tip end side of the insertion portion and expands and contracts by supplying and sucking air;

a second balloon which is placed at a tip end side of the insertion auxiliary member and expands and contracts by supplying and sucking air;

a holding device which has an insertion auxiliary member holder for holding an insertion auxiliary member, an endoscope holder for holding a hand operation portion of the endoscope, a first driving device for moving the endoscope holder in an insertion direction or a withdrawal direction, and a second driving device for moving the insertion auxiliary member in an insertion direction or a withdrawal direction;

a first air supplying and sucking device for supplying and sucking air to and from the first balloon;

a second air supplying and sucking device for supplying and sucking air to and from the second balloon;

an operation device; and a control device which controls, in accordance with operation of the operation device, driving of the first air supplying and sucking device, the second air supplying and sucking air, the first driving device, and the second driving device, wherein the operation device includes a step advancement instruction device which instructs advancing of steps so that the predetermined operation steps advance in sequence and wherein the predetermined operation steps comprise:

a first step of moving, in accordance with a next instruction by the step advancement instruction device to advance steps, the insertion portion in the insertion direction by a predetermined amount by driving the first driving device to move the endoscope holder in the insertion direction by a predetermined amount;

a second step of expanding, in accordance with a next instruction by the step advancement instruction device to advance steps, the first balloon by driving the first air supplying and sucking device to supply air to the first balloon;

a third step of contracting, in accordance with a next instruction by the step advancement instruction device to advance steps, the second balloon by driving the second air supplying and sucking device to suck air from the second balloon;

a fourth step of moving, in accordance with a next instruction by the step advancement instruction device to advance steps, the insertion auxiliary member in the insertion direction by a predetermined amount by driving the second driving device to move the insertion auxiliary member holder in the insertion direction by a predetermined amount;

a fifth step of expanding, in accordance with a next instruction by the step advancement instruction device to advance steps, the second balloon by driving the second air supplying and sucking device to supply air to the second balloon;

a sixth step of moving, in accordance with a next instruction by the step advancement instruction device to advance steps, the insertion portion and the insertion auxiliary member in a direction opposite to the insertion direction by a predetermined amount by driving the first and second driving devices to move the endoscope holder and the insertion auxiliary member holder in a direction opposite to the insertion direction by a predetermined amount; and a seventh step of contracting, in accordance with a next instruction by the step advancement instruction device to advance steps, the first balloon by driving the first air supplying and sucking device to suck air from the first balloon;

a eighth step of moving, in accordance with a next instruction by the step advancement instruction device to advance steps, the insertion portion in the insertion direction by a predetermined amount by driving the first driving device to move the endoscope holder in the insertion direction by a predetermined amount;

where after the eighth step, the second to eighth steps are repeated in accordance with a next instruction by the step advancement instruction device to advance steps; and wherein the control device controls, in accordance with the instruction by the step advancement instruction device, driving of the first air supplying and sucking device, the second air supplying and sucking air, the first driving device, and the second driving device, so that the operation steps advance in sequence.

5. The balloon control apparatus according to claim 4, wherein the operation device includes a mode switching device for switching operation mode to manual operation mode, a first air supplying and sucking instruction device, a second air supplying and sucking instruction device, a first movement instruction device for instructing moving the endoscope holder, and a second movement instruction device for instructing movement of the insertion auxiliary member holder, and when operation mode is switched to the manual operation mode, the control device controls, in accordance with instruction by the first air supplying and sucking instruction device, the second air supplying and sucking instruction device, the first driving device, and the second driving device, driving of the first air supplying and sucking device, the second air supplying and sucking device, the first driving device, and the second driving device.

6. The balloon control apparatus according to claim 4, wherein the predetermined operation steps further comprises a step of expanding, in accordance with a next instruction by the step advancement instruction device to advance steps, the balloon for insertion auxiliary member by driving the air supplying and sucking device for insertion auxiliary member to supply air to the balloon for insertion auxiliary member, as a step previous to the first step.

* * * * *